(12) United States Patent
Miller et al.

(10) Patent No.: US 10,932,717 B2
(45) Date of Patent: Mar. 2, 2021

(54) SUNSCREEN FORMULATION AND SYSTEMS FOR SUN PROTECTION AND RELATED METHODS OF USE

(71) Applicants: Zane Bowman Allen Miller, Redmond, WA (US); Susan Halpern, Clark, NJ (US); John Hix, Redmond, WA (US)

(72) Inventors: Zane Bowman Allen Miller, Redmond, WA (US); Susan Halpern, Clark, NJ (US); John Hix, Redmond, WA (US)

(73) Assignee: L'Oreal, Paris (FR)

( * ) Notice: Subject to any disclaimer, the term of this patent is extended or adjusted under 35 U.S.C. 154(b) by 759 days.

(21) Appl. No.: 15/799,952

(22) Filed: Oct. 31, 2017

(65) Prior Publication Data
US 2019/0125258 A1 May 2, 2019

(51) Int. Cl.
*A61B 5/00* (2006.01)
*A61Q 17/04* (2006.01)
*A61K 8/49* (2006.01)
*A61K 8/34* (2006.01)
*A61B 90/00* (2016.01)

(52) U.S. Cl.
CPC ............ *A61B 5/4848* (2013.01); *A61K 8/347* (2013.01); *A61K 8/4953* (2013.01); *A61Q 17/04* (2013.01); *A61B 5/0077* (2013.01); *A61B 5/441* (2013.01); *A61B 5/742* (2013.01); *A61B 90/39* (2016.02); *A61B 2090/397* (2016.02)

(58) Field of Classification Search
CPC ..... A61B 5/0077; A61B 5/441; A61B 5/4848; A61B 5/742; A61B 90/39; A61B 2090/397; A61K 8/347; A61K 8/4953; A61Q 17/04; G01N 33/5097
See application file for complete search history.

(56) References Cited

U.S. PATENT DOCUMENTS

| 5,087,445 A | * | 2/1992 | Haffey | A61K 8/445 424/59 |
| 2013/0300850 A1 | * | 11/2013 | Millikan | G01J 3/513 348/77 |
| 2015/0041663 A1 | * | 2/2015 | Oliver | G01J 1/0219 250/372 |

FOREIGN PATENT DOCUMENTS

WO   WO-2014040177 A1 *  3/2014   ............ A61Q 19/08

* cited by examiner

*Primary Examiner* — Boniface N Nganga
(74) *Attorney, Agent, or Firm* — Christensen O'Connor Johnson Kindness PLLC

(57) ABSTRACT

Sunscreen formulations and systems for sun protection and related methods of use are described herein.

10 Claims, 17 Drawing Sheets

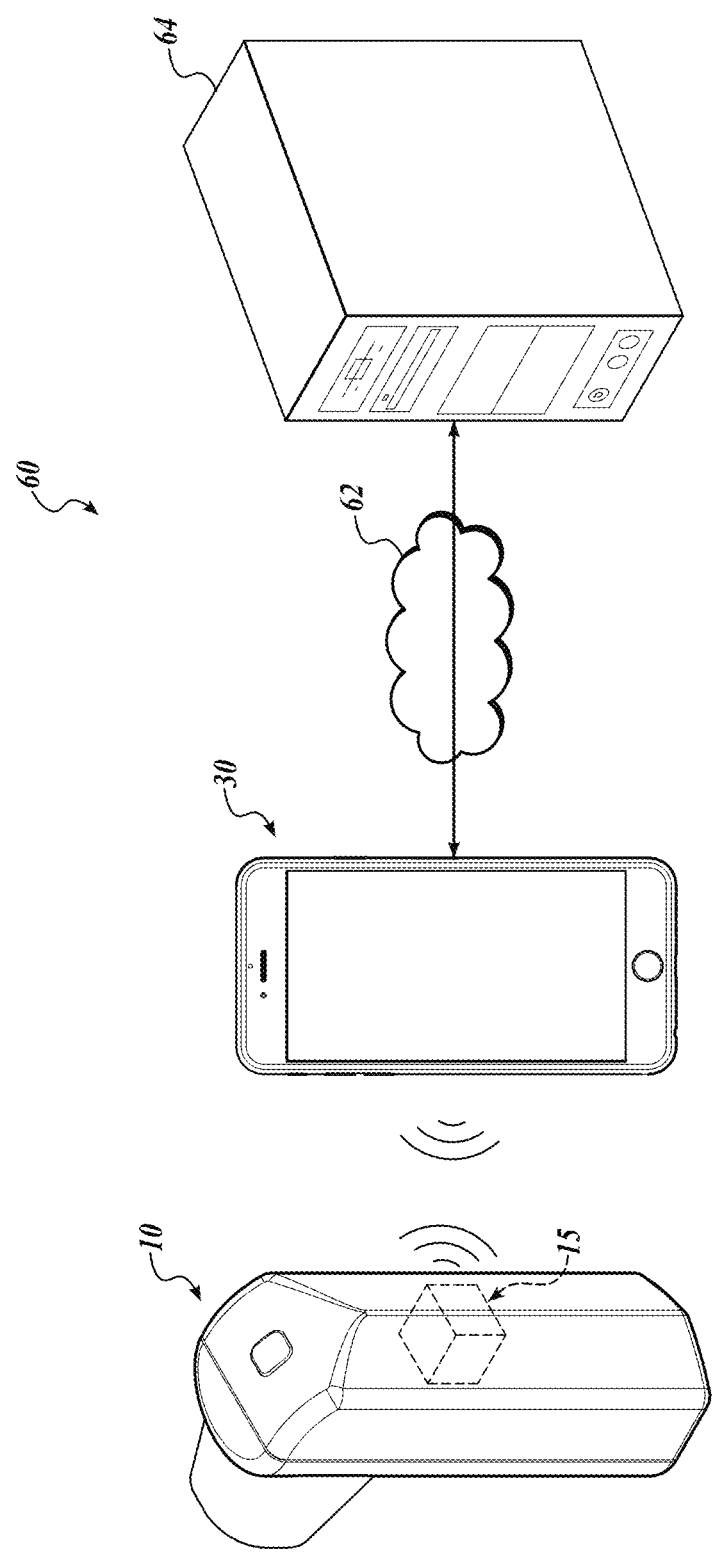

SUNSCREEN FORMULATION AND SYSTEMS FOR SUN PROTECTION AND RELATED METHODS OF USE

SUMMARY

In an aspect, the present disclosure provides a sunscreen formulation for application to skin of a subject, the sunscreen formulation comprising: an active ingredient configured to absorb ultraviolet electromagnetic radiation; and a marker configured to absorb ultraviolet electromagnetic radiation and configured to generate a detectable signal in response to the marker absorbing ultraviolet electromagnetic radiation.

In another aspect, the present disclosure provides a system for analyzing ultraviolet protection of skin of a subject, the system comprising: a sunscreen formulation for application to skin of a subject, the sunscreen formulation comprising: an active ingredient configured to absorb ultraviolet electromagnetic radiation; and a marker configured to absorb ultraviolet electromagnetic radiation and configured to generate a detectable signal in response to the marker absorbing ultraviolet electromagnetic radiation; an interrogator configured to generate interrogation data based on the detectable signal generated by the marker in response to ultraviolet electromagnetic radiation absorbed by the marker; and an analyzer communicatively coupled to the interrogator and configured to receive the interrogation data from the interrogator, wherein the analyzer is configured to generate an ultraviolet absorption analysis based at least in part on the interrogation data.

In another aspect, the present disclosure provides a system for analyzing ultraviolet protection for skin of a subject, the system comprising: marker acquisition means for receiving sunscreen marker information responsive to a marker absorbing ultraviolet electromagnetic radiation; ultraviolet analysis means for generating an ultraviolet absorption analysis based at least in part on the sunscreen marker information; and protection display means for generating a virtual display including one or more instances indicative of an ultraviolet protection status of a user, ultraviolet protection recommendation information, exposure information, or sunscreen coverage information analysis based at least in part on the ultraviolet absorption analysis.

In accordance with any of the embodiments disclosed herein, the active ingredient is configured to absorb light in a first range of ultraviolet electromagnetic radiation; and wherein the marker is configured to absorb light in a second range of ultraviolet electromagnetic radiation overlapping at least in part with the first range of electromagnetic radiation.

In accordance with any of the embodiments disclosed herein, the marker is photo-luminescent and the detectable signal includes electromagnetic radiation emitted by the marker.

In accordance with any of the embodiments disclosed herein, the marker has a first absorbance spectrum before absorbing ultraviolet electromagnetic radiation and a second absorbance spectrum after absorbing ultraviolet electromagnetic radiation, and wherein the first absorbance spectrum is different from the second absorbance spectrum.

In accordance with any of the embodiments disclosed herein, the marker generates the detectable signal at a first level in response to the sunscreen formulation absorbing a first amount of ultraviolet electromagnetic radiation and generates the detectable signal at a second level greater than the first level in response to the sunscreen formulation absorbing additional ultraviolet electromagnetic radiation.

In accordance with any of the embodiments disclosed herein, the sunscreen formulation includes a second active ingredient configured to absorb ultraviolet electromagnetic radiation.

In accordance with any of the embodiments disclosed herein, the sunscreen formulation includes a second marker configured to absorb ultraviolet electromagnetic radiation and configured to generate a second detectable signal in response to the second marker absorbing ultraviolet electromagnetic radiation. In accordance with any of the embodiments disclosed herein, the second active ingredient is configured to absorb light in a third range of ultraviolet electromagnetic radiation, and wherein the second marker configured to absorb light in a fourth range of ultraviolet electromagnetic radiation at least partially overlapping with the third range of electromagnetic radiation. In accordance with any of the embodiments disclosed herein, the second detectable signal is different from the first detectable signal.

In accordance with any of the embodiments disclosed herein, the detectable signal includes light emitted by the marker in a third range of electromagnetic radiation and the interrogator includes a sensor including a photo-detector configured to absorb the light emitted by the marker and a band-pass filter configured to filter wavelengths that are outside of the third range of electromagnetic radiation.

In accordance with any of the embodiments disclosed herein, the recommendation for further ultraviolet protection of the skin of a subject includes a recommended area of application of a sunscreen formulation on the skin of a subject.

In accordance with any of the embodiments disclosed herein, the ultraviolet adsorption analysis includes at least a recommendation for further ultraviolet protection of the skin of a subject, the system further comprising an output communicatively coupled to the analyzer and configured to receive the ultraviolet absorption analysis and to output the recommendation for further ultraviolet protection of the skin of a subject.

In accordance with any of the embodiments disclosed herein, the output is configured to display an image of the skin of a subject with the recommended area of application of sunscreen highlighted in a particular color.

In accordance with any of the embodiments disclosed herein, the marker acquisition means includes at least one of a transceiver, a transmitter, and a receiver operably coupled to an interrogator having at least one electromagnetic energy transducer configured to acquire sunscreen marker information responsive to a marker absorbing ultraviolet electromagnetic radiation.

In accordance with any of the embodiments disclosed herein, the at least one electromagnetic energy transducer is chosen from an ultraviolet sensor, an optical sensor, a radiation sensor, and a camera.

In accordance with any of the embodiments disclosed herein, the ultraviolet analysis means includes sunscreen marker information stored in memory and at least one processor configured to determine at least one of an ultraviolet protection status of a user, ultraviolet protection recommendation information, exposure information, and sunscreen coverage information based on one or more inputs indicative of sunscreen marker information.

In accordance with any of the embodiments disclosed herein, the protection display means includes a touch screen display operably coupled to a processor configured to generate a virtual representation on the touch screen display including one or more instances indicative of an ultraviolet protection status of a user, ultraviolet protection recommendation information, exposure information, or sunscreen coverage information analysis based at least in part on the ultraviolet absorption analysis.

In another aspect, the present disclosure provides a method of analyzing ultraviolet protection for skin of a subject, the method comprising: receiving, by an analyzer from an interrogator, interrogation data generated by the interrogator, interrogation data based on sensed detectable signal generated by a marker in a sunscreen formulation in response to the marker absorbing ultraviolet electromagnetic radiation; and generating, by the analyzer, an ultraviolet absorption analysis based at least in part on the interrogation data.

In accordance with any of the embodiments disclosed herein, generating the ultraviolet analysis includes generating the recommendation for further ultraviolet protection of the skin of a subject based on an amount of the detectable signal sensed by the interrogator.

In accordance with any of the embodiments disclosed herein, generating the ultraviolet analysis includes generating the recommendation for further ultraviolet protection of the skin of a subject based on a comparison of an amount of the detectable signal sensed by the interrogator at first time and an amount of the detectable signal sensed by the interrogator at second time after the first time.

This forgoing summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

FIGS. 10A and 10B illustrate systems, in accordance with an aspect of the disclosure, including an interrogator, an analyzer, a communication network, and a remote computing device.

Figure 1A:
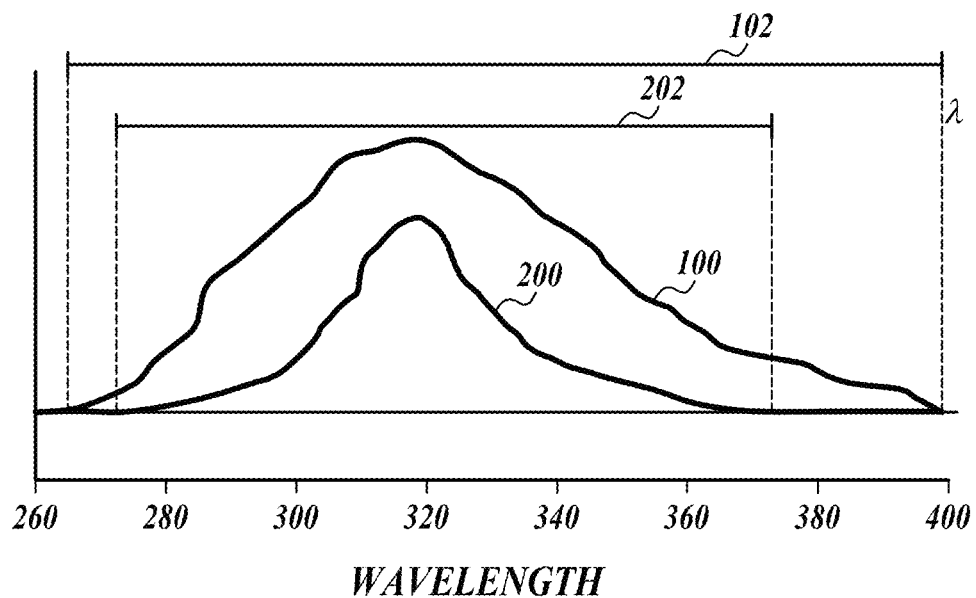
FIG. 1A illustrates the absorbance spectra of an active ingredient and a marker in accordance with an aspect of the disclosure.

Aspects and many of the attendant advantages of the claimed subject matter will become more readily appreciated as the same become better understood by reference to the following detailed description, when taken in conjunction with the accompanying drawings.

The detailed description set forth below in connection with the appended drawings, where like numerals reference like elements, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

DETAILED DESCRIPTION

The present disclosure relates generally to sunscreen formulations for application to skin of a subject, systems including the sunscreen formulations, and related methods of use. Generally described, sunscreen formulations, such as lotions, creams, oils, sprays, foams, and the like, include an active ingredient configured to absorb ultraviolet electromagnetic radiation in order to prevent the skin of a subject from absorbing such harmful ultraviolet electromagnetic radiation.

With instances of skin cancer and other skin-related afflictions increasing, awareness about skin protection has also been increasing. Skin protection often comes in the form of skin covering, such as clothing and accessories (e.g., hats), and skin treatments, such as sunscreen. Skin protection can limit or prevent harm to skin from certain kinds of exposure, such as exposure to ultraviolet (UV) electromagnetic energy (e.g., sunlight), which has a wavelength in a range from 10 nm to 400 nm. However, many individuals do not understand the coverage and strength of their chosen form(s) of skin protection, and remain vulnerable to exposure when they believe that they are protected.

Many individuals have difficulty verifying coverage and strength of skin treatments, such as sunscreen. Because most sunscreen formulations are not visible when they are applied, it is difficult for individuals to discern between areas of their skin where sunscreen has been applied and areas of their skin where sunscreen has not been applied. In addition, certain types of sunscreen applicators give the illusions of proper and complete coverage when there is in fact little to no coverage. For example, spray sunscreen applicators often give users the impression that spraying alone provides complete coverage, when the sprayed sunscreen does not provide proper exposure until it is worked into the skin by hand. Areas of missed or limited skin treatment coverage can result in immediate effects, such as sunburns in the exposed areas, and the long-term effects, such as increased possibility of developing skin cancer, prematurely aging the skin, and creating areas of hyperpigmentation.

Another issue with skin treatments is the deterioration of the skin treatment effectiveness over time. The rate at which the effectiveness of skin treatment deteriorates or varies based on a number of factors. These factors include one or more of the degradation of electromagnetic radiation filters in the skin treatment either before or after application, wearing away of the skin treatment from certain activities (e.g., swimming, exercising, physical activity, etc.), and physiological effects of the person on whom the skin treatment has been applied (e.g., sweat, body temperature, etc.). A person who has applied a skin treatment typically is unable to determine the effectiveness of the skin treatment at the time of application or at any time thereafter. Thus, such a person typically does not know whether and when to apply additional skin treatment to ensure sufficient protection.

Existing ratings of skin treatments are imperfect metrics of skin protection. In the United States, sunscreen skin treatments are given an SPF ("sun protection factor") value. The SPF value is intended as a measure of the fraction of sunburn-producing UV rays that reach the skin (e.g., "SPF 30" indicates that 1/30th of sunburn-producing UV rays reach the skin). However, this reading is imprecise for a number of reasons. In one example, the amount of exposure to UV rays that produces sunburns varies from individual to individual. In another example, the amount of protection provided by any skin treatment varies based on the amount and uniformity of application of the skin treatment to the skin. In another example, visible skin damage is typically caused by UV radiation type A (UVA), which has a wavelength in the range of 315 nm to 400 nm, and SPF values are based on visible damage caused to skin. However, nonvisible damage to skin is caused by exposure to other sources of electromagnetic radiation, such as UV radiation type B (UVB), which has a wavelength in the range of 280 nm to 315 nm, other UV electromagnetic radiation, or non-UV electromagnetic radiation. Thus, some skin treatments may have high SPF values, indicating that they protect well against UVA, while offering little to no protection from UVB or other forms of electromagnetic radiation.

Based on these considerations, there is a need for aiding individuals in understanding their exposure to skin-harming electromagnetic radiation. This understanding may include one or more of understanding a current level of protection from skin-harming electromagnetic radiation, understanding a rate at which the level of protection is degrading, understanding an expected time at which skin protection should be adjusted or reapplied, understanding an exposure to skin-harming electromagnetic radiation over a period of time, or any other understanding of the state or effect of skin-harming electromagnetic radiation.

To that end, the following discussion provides examples of, inter alia, sunscreen formulations including an active ingredient configured to absorb ultraviolet electromagnetic radiation; and at least one marker configured to absorb ultraviolet electromagnetic radiation and configured to generate a detectable signal in response to the marker(s) absorbing ultraviolet electromagnetic radiation. As will be described in more detail below, the presence or increase in intensity of the detectable signal is indicative of the active ingredient failing to absorb at least a portion of electromagnetic radiation impinging upon the sunscreen formulation. Further, as will be described in more detail below, an increase in the intensity or level of the detectable signal is indicative of the active ingredient degrading or otherwise losing efficacy in absorbing ultraviolet radiation. In that regard, as will be described in more detail below, detection of the detectable signal can be used to generate a recommendation for further ultraviolet protection of the skin of a subject.

In the following description, numerous specific details are set forth in order to provide a thorough understanding of one or more embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein.

In an aspect, the present disclosure provides sunscreen formulation for application to skin of a subject, the sunscreen formulation comprising: an active ingredient configured to absorb ultraviolet electromagnetic radiation; and a marker configured to absorb ultraviolet electromagnetic radiation and configured to generate a detectable signal in response to the marker absorbing ultraviolet electromagnetic radiation.

The active ingredient can be any active ingredient configured to absorb ultraviolet electromagnetic radiation. In an embodiment, the active ingredient is configured to absorb ultraviolet electromagnetic radiation having a wavelength between about 100 nm and about 400 nm. In an embodiment, the active ingredient is configured to absorb ultraviolet electromagnetic radiation having a wavelength between about 315 nm and about 400 nm. In an embodiment, the active ingredient is configured to absorb ultraviolet electromagnetic radiation having a wavelength between about 280 nm and about 315 nm. In an embodiment, the active ingredient is configured to absorb ultraviolet electromagnetic radiation having a wavelength between both about 315 nm and about 400 nm and about 280 nm and about 315 nm. In an embodiment, the active ingredient is configured to absorb ultraviolet electromagnetic radiation having a wavelength between about 100 nm and about 280 nm.

In an embodiment, the active ingredient is chosen from p-aminobenzoic acid, padimate O, phenylbenzimidazole sulfonic acid, cinoxate, dioxybenzone, oxybenzone, homosalate, menthyl anthranilate, octocrylene, octyl methoxycinnamate, octyl salicylate, sulisobenzone, trolamine salicylate, avobenzone, ecamsule, titanium dioxide, and zinc oxide.

In an embodiment, the active ingredient is chosen from 4-methylbenzylidene camphor, tinosorb M, tinosorb S, tinosorb A2B, neo heliopan AP, mexoryl XL, benzophenone-9, uvinul T 150, uvinul A Plus, uvasorb HEB, parsol SLX, and amiloxate.

In an embodiment, the active ingredient is chosen from avobenzone, octisalate, homosalate, octocrylene, oxybenzone, octinoxate, mexoryl SX, mexoryl XL, $TiO_2$, and ZnO.

In an embodiment, the sunscreen formulations described herein include one or more active ingredients each configured to absorb ultraviolet electromagnetic radiation. In an embodiment, the sunscreen formulations described herein include one, two, three, or more active ingredients. In an embodiment and as described further herein, each of the active ingredients of the sunscreen formulation absorb a different range of ultraviolet electromagnetic radiation.

In an embodiment, the sunscreen formulation includes one or more active ingredients at a level sufficient to provide protection from harmful UV light when applied to the skin of a subject. In an embodiment, the sunscreen formulation includes one or more active ingredients at a level sufficient to have an SPF of between about 5 and about 100. In an embodiment, the sunscreen formulation includes one or more active ingredients at a level sufficient to have an SPF of between about 15 and about 75. In an embodiment, the sunscreen formulation includes one or more active ingredients at a level sufficient to have an SPF of between about 30 and about 50. One of skill in the art will readily appreciate the amount or level of a particular active ingredient to include in the sunscreen formulations described herein to achieve a particular level of protection from UV light, such as a particular SPF.

As described herein above, embodiments of the sunscreen formulation include a marker configured to absorb ultraviolet electromagnetic radiation and configured to generate a detectable signal in response to the marker absorbing ultraviolet electromagnetic radiation.

The marker can be any compound or group of compounds configured to absorb ultraviolet electromagnetic radiation and configured to generate a detectable signal in response to the marker absorbing ultraviolet electromagnetic radiation.

In an embodiment, the marker is at a concentration insufficient to absorb substantial levels of ultraviolet electromagnetic radiation and, accordingly, is not an active ingredient.

In an embodiment, the marker is photo-luminescent and the detectable signal includes electromagnetic radiation emitted by the marker. In an embodiment, the marker is fluorescent. In an embodiment, the electromagnetic radiation emitted by the marker includes ultraviolet electromagnetic radiation. In an embodiment, the electromagnetic radiation emitted by the marker includes visible electromagnetic radiation.

In an embodiment, the marker is chosen from curcurmin, luteolin, piceatannol, caffeic acid, catechin (hydrate), baicalein, epigallocatechin gallate, genistein, silybin, resveratrol, apigenin, chrysin, hesperetin, quinine, myricetin, ellagic acid, naringin, rutin, trihydrate, caffeine, andrographolide, and lycopene.

In an embodiment and as discussed further herein, the sunscreen formulations include two or more markers each configured to generate a detectable signal in response to absorbing ultraviolet electromagnetic radiation.

In an embodiment, the marker provides a benefit to the skin of the user beyond providing a marker of UV light absorption. For example, in an embodiment, the marker is caffeine, which has been shown to have antioxidant properties, especially when skin is exposed to UV light. In an embodiment, the marker is resveratrol, which has been shown to have antioxidant properties.

In an embodiment, the active ingredient is configured to absorb light in a first range of ultraviolet electromagnetic radiation; and the marker is configured to absorb light in a second range of ultraviolet electromagnetic radiation overlapping at least in part with the first range of electromagnetic radiation. In that regard, attention is directed to FIG. 1A, wherein the ultraviolet absorbance spectrum of an example active ingredient in accordance with an embodiment of the disclosure and the ultraviolet absorbance spectrum of an example marker in accordance with an embodiment of the disclosure are illustrated. In the illustrated embodiment, the active ingredient absorbs ultraviolet light represented by ultraviolet absorbance spectra 100 with absorbance features within a first range 102 of ultraviolet radiation. Likewise, the marker absorbs ultraviolet light represented by absorbance spectra 200 with absorbance features within a second range 202 of ultraviolet radiation. As shown, the second range 202 of ultraviolet electromagnetic radiation overlaps at least in part with the first range 102 of ultraviolet electromagnetic radiation. In this regard, the active ingredient generally shields the marker from ultraviolet electromagnetic radiation, thereby preventing or limiting the marker from generating the detectable signal.

Figure 1B:
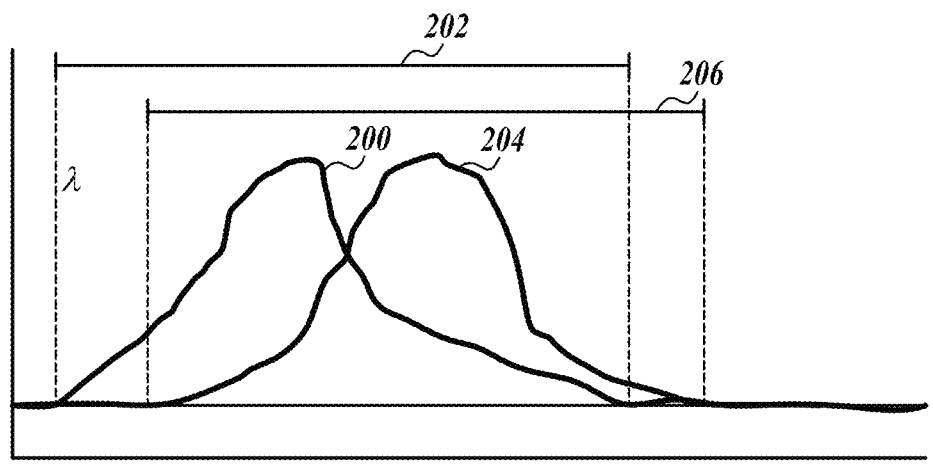
FIG. 1B illustrates the absorbance spectrum and the emission spectrum of a marker in accordance with an aspect of the disclosure.

In an embodiment, the marker is photo-luminescent and the detectable signal includes electromagnetic radiation emitted by the marker. In that regard, attention is directed to FIG. 1B, where the absorbance and emission spectra of a representative marker are illustrated. In the illustrated embodiment, the marker absorbs ultraviolet light represented by absorbance spectrum 200 with absorbance features in a second range 202 of ultraviolet electromagnetic radiation. Further, the marker generates a detectable signal that includes emitted light represented by emission spectra 204 with emission features in a range 206 of electromagnetic radiation, wherein ranges 202 and 206 are different.

Figure 4A:
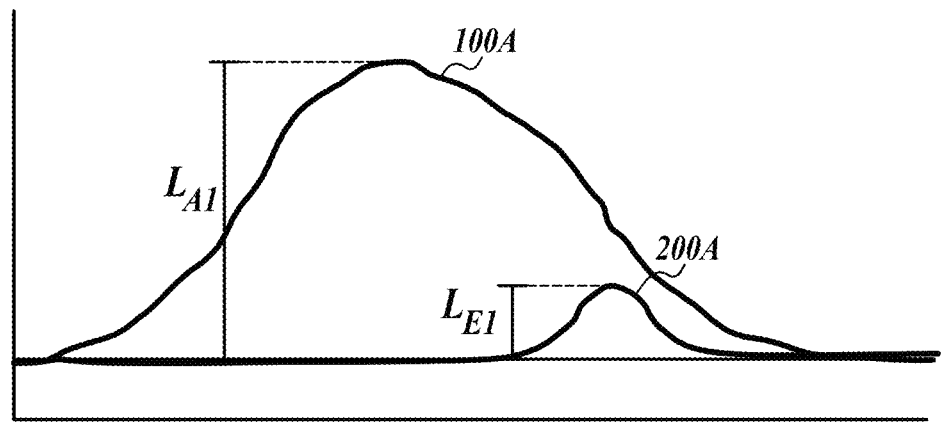
FIG. 4A illustrates the absorbance spectrum of an active ingredient and the emission spectrum of a marker in accordance with an aspect of the disclosure after a sunscreen formulation containing the active ingredient and the marker has absorbed a first amount of ultraviolet electromagnetic radiation.
Figure 4B:
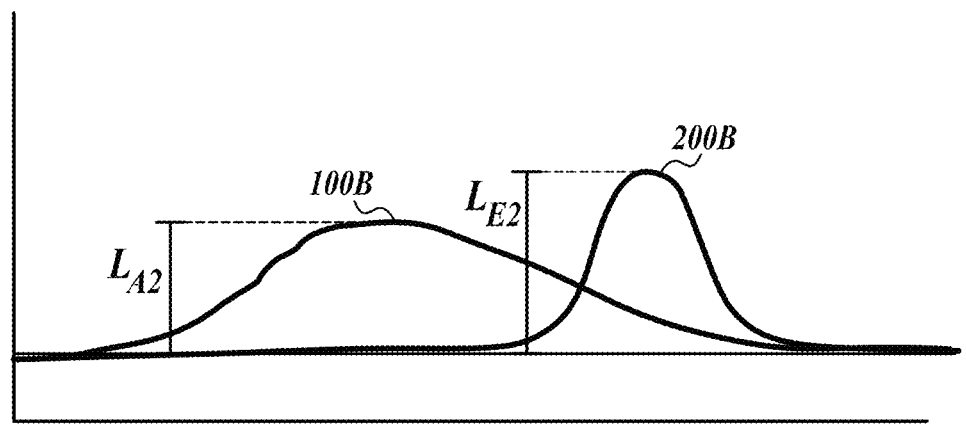
FIG. 4B illustrates the absorbance spectrum of the active ingredient of FIG. 4A and the emission spectrum of the marker of FIG. 4A after the sunscreen formulation of FIG. 4A has absorbed a second amount of ultraviolet electromagnetic radiation.

In an embodiment, the marker generates the detectable signal at a first level in response to the sunscreen formulation absorbing a first amount of ultraviolet electromagnetic radiation and generates the detectable signal at a second level greater than the first level in response to the sunscreen formulation absorbing additional ultraviolet electromagnetic radiation. In that regard, attention is directed to FIGS. 4A and 4B, where representative active ingredient absorbance spectra and marker emission spectra are illustrated. As illustrated in FIG. 4A, at a first time, such as after an initial exposure to sunlight, the active ingredient absorbs ultraviolet light represented by absorbance spectra 100A having an absorbance maximum, $L_{A1}$ and the marker generates a detectable signal represented in the illustrated embodiment by emission spectra 200A having an emission maximum, $L_{E1}$. After absorbing an additional amount of ultraviolet electromagnetic radiation, the active ingredient has an absorbance spectra 100B with absorbance maximum, $L_{A2}$, which is less than absorbance maximum $L_{A1}$, as illustrated in FIG. 4B. Because the active ingredient is now absorbing less ultraviolet radiation, the marker absorbs more ultraviolet electromagnetic radiation. This is also reflected in FIG. 4B, where the marker has an emission spectra 200B with an emission maximum, $L_{E2}$, which is greater than emission maximum $L_{E1}$. As described further herein, in certain embodiments it can be inferred that when the marker generates the detectable signal at a second level greater than the first level in response to the sunscreen formulation absorbing additional ultraviolet electromagnetic radiation that the active ingredient is absorbing less ultraviolet electromagnetic radiation. Furthermore, and as described further herein, such an increase in the level of detectable signal can be used in analyzing ultraviolet protection for skin of a subject and in generating a recommendation for further ultraviolet protection of the skin of a subject.

Figure 3:
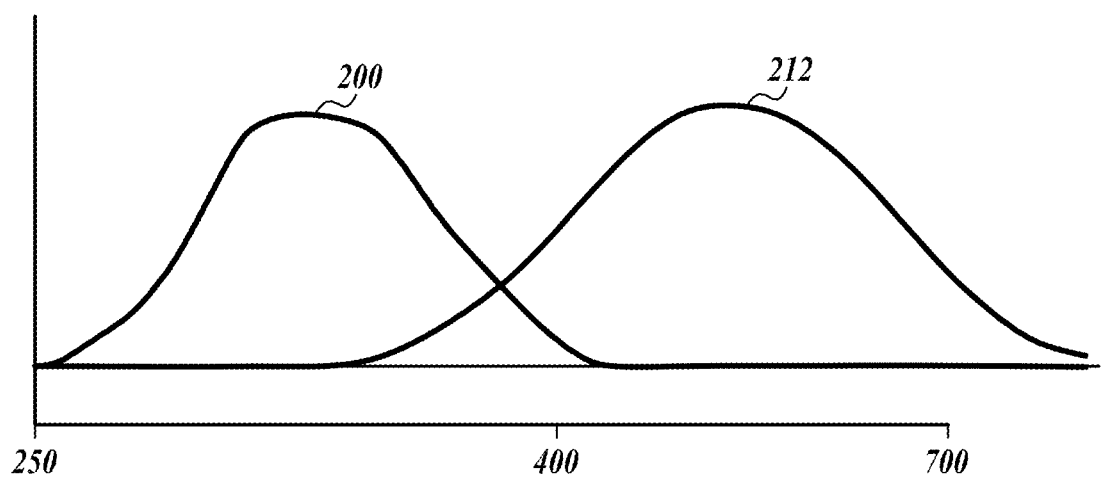
FIG. 3 illustrates the absorbance spectrum of a marker in accordance with an aspect of the disclosure after absorbing a first amount of or no ultraviolet electromagnetic radiation and the absorbance spectrum of the marker after absorbing a second amount of ultraviolet electromagnetic radiation.

In an embodiment, the marker has a first absorbance spectrum before absorbing ultraviolet electromagnetic radiation and a second absorbance spectrum after absorbing ultraviolet electromagnetic radiation, and wherein the second absorbance spectrum is different from the first absorbance spectrum. In this regard, attention is directed to FIG. 3, where example absorbance spectra of a marker according to an embodiment of the present disclosure is illustrated. In the illustrated embodiment, the marker has a first absorbance spectrum 200 before absorbing ultraviolet electromagnetic radiation having absorbance maximum in the ultraviolet range of electromagnetic radiation. The marker has a second absorbance spectrum 212 after absorbing ultraviolet electromagnetic radiation, wherein the absorbance spectrum 212 is different from the absorbance spectrum 200. In an embodiment, the second absorbance spectrum has an absorbance maximum in the visible range of electromagnetic radiation. In this regard, in certain embodiments the sunscreen formulations described herein have a first color or no visible color before absorbing ultraviolet electromagnetic radiation and a second color, such as a color in the visible range, after absorbing ultraviolet electromagnetic radiation. Accordingly, in certain embodiments the detectable signal is a color change wherein, when in use, such sunscreen formulations acquire, for example, a visible color as the active ingredient degrades and the marker absorbs ultraviolet electromagnetic radiation.

Figure 2A:
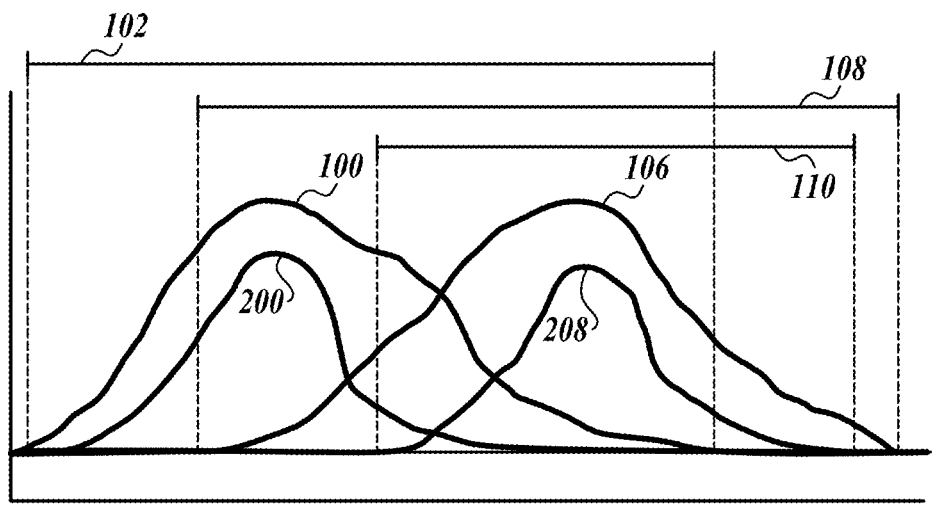
FIG. 2A illustrates the absorbance spectra of two active ingredients and the absorbance spectra of two markers in accordance with an aspect of the disclosure.

In an embodiment, the sunscreen formulations described herein include a second active ingredient configured to absorb ultraviolet electromagnetic radiation. In this regard, attention is directed to FIG. 2A where an absorbance spectrum of a first active ingredient and an absorbance spectrum of a second active ingredient in accordance with an embodiment of the disclosure are illustrated. In the illustrated embodiment, the first active ingredient absorbs ultraviolet electromagnetic radiation represented by a first absorbance spectrum 100 and the second active ingredient absorbs ultraviolet electromagnetic radiation represented by a second absorbance spectrum 106. In an embodiment and as illustrated in FIG. 2A, the first active ingredient absorbs ultraviolet electromagnetic radiation in a first range 102 and the second active ingredient is configured to absorb light in a third range 108 of ultraviolet electromagnetic radiation. In an embodiment, the third range 108 of ultraviolet electromagnetic radiation is different from the first range 102 of ultraviolet electromagnetic radiation. Accordingly, in an embodiment, the first active ingredient absorbs light in, for example, the UVA region and the second active ingredient absorbs light, for example, in the UVB region.

In an embodiment, the sunscreen formulations described herein further include a second marker configured to absorb ultraviolet electromagnetic radiation and configured to generate a second detectable signal in response to the second marker absorbing ultraviolet electromagnetic radiation. Further, in certain embodiments, the second marker is configured to absorb light in a fourth range 110 of ultraviolet electromagnetic radiation at least partially overlapping with the third range 108 of electromagnetic light.

Referring still to FIG. 2A, the first marker has an absorbance spectrum 200 at least partially overlapping with the absorbance spectrum 100 of the first active ingredient and the second marker has an absorbance spectrum 208 at least partially overlapping with the absorbance spectrum 106 of the second active ingredient. In this regard and as discussed further herein, when present at sufficient levels the first and second active ingredients prevent or mitigate the first and second markers, respectively, from generating first and second detectable signals. Analogously, the first and second markers generate first and second detectable signals, respectively, when the first and second active ingredients fail absorb ultraviolet electromagnetic radiation incident upon the sunscreen formulation and absorbed by the first and second markers.

Figure 2B:
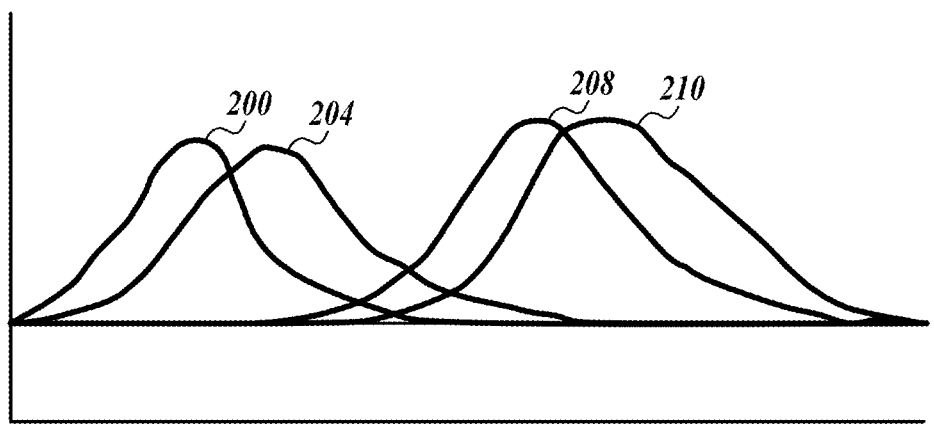
FIG. 2B illustrates the absorbance spectra and the emission spectra of two markers in accordance with an aspect of the disclosure.

Further, in certain embodiments, the second marker is configured to absorb ultraviolet electromagnetic radiation and configured to generate a second detectable signal in response to the second marker absorbing ultraviolet electromagnetic radiation. In that regard, attention is directed to FIG. 2B where emission spectra and absorbance spectra of a first and a second marker according to the embodiments of disclosure are illustrated. As illustrated, the first marker absorbs electromagnetic radiation represented by a first absorbance spectrum 200 and generates a first detectable signal including emitted electromagnetic radiation represented by a first emission spectrum 204. Likewise, the second marker absorbs ultraviolet light as represented by second absorbance spectrum 208 and generates of second detectable signal in response absorbing ultraviolet light as represented by second emission spectrum 210. In an embodiment, the second detectable signal is different from the first detectable signal. In the illustrated embodiment, the first emission spectrum 204 has an emission maximum different from the maximum of the second emission spectrum 210. In this regard and according to certain embodiments described herein, the sunscreen formulation is configured to provide independently two detectable signals in response to two active ingredients degrading or otherwise failing to absorb ultraviolet electromagnetic radiation. Accordingly, in certain embodiments, the sunscreen formulation is configured to provide detectable signals indicative of a sunscreen formulation failing to provide, for example, protection to the skin of a subject from UVB light and/or UVA light.

In an embodiment, the sunscreen formulations described herein are configured to be applied to the skin of a subject. In an embodiment, the sunscreen formulations described herein are in the form of a lotion, a cream, an oil, a spray, a foam, and the like, and are generally configured to coat a portion of skin. In an embodiment, the active ingredient and the marker are intermixed in the sunscreen formulation.

In an embodiment, the sunscreen formulations described herein include inactive ingredients such as moisturizers, emulsifiers, preservatives, solvents, and the like.

Figure 5:
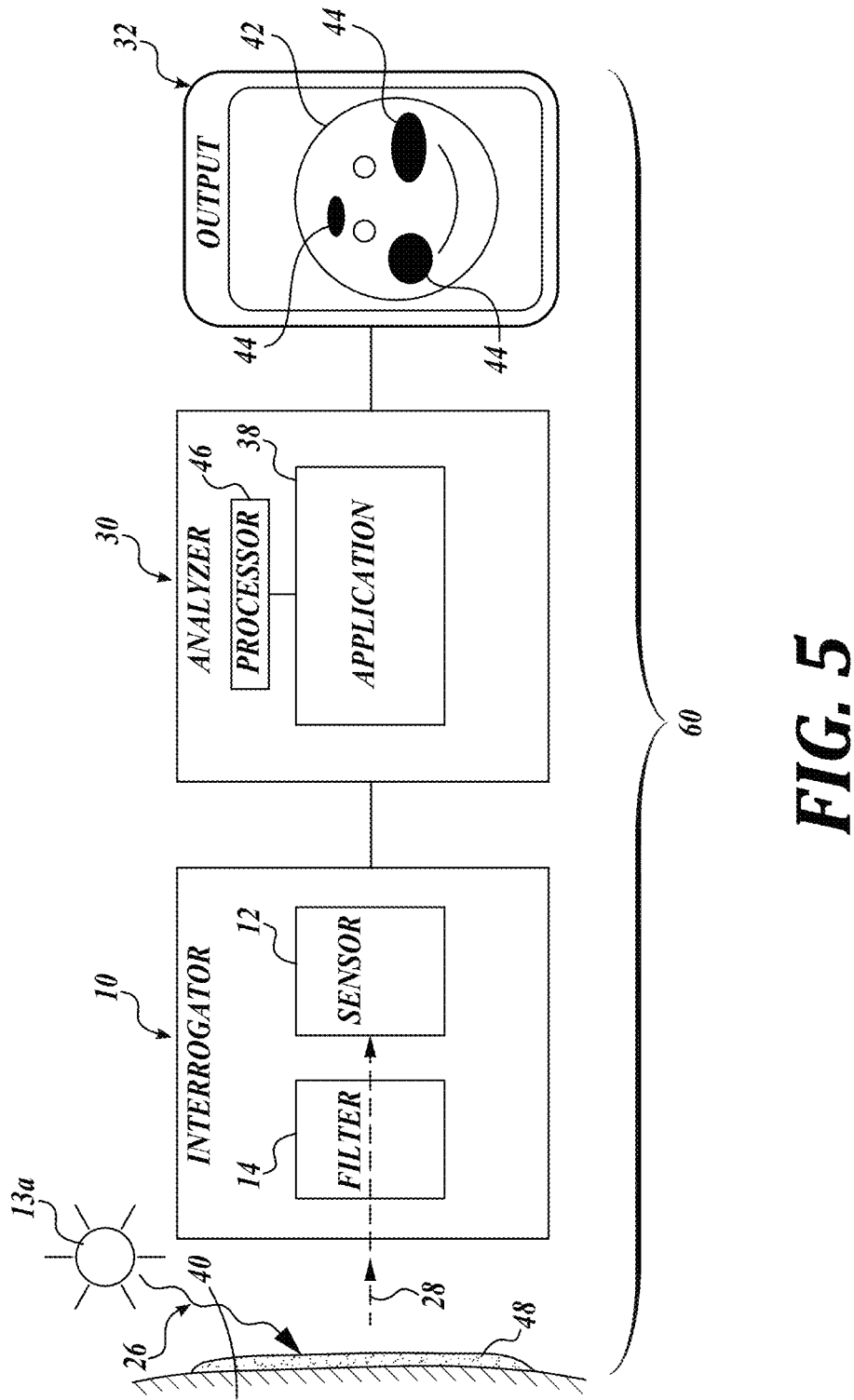
FIG. 5 schematically illustrates a system in accordance with an aspect of the disclosure.

In another aspect, the present disclosure provides a system for analyzing ultraviolet protection of the skin of a subject. In that regard, FIG. 5 is a schematic illustration of a representative system 60 in accordance with an aspect of the disclosure. In the illustrated embodiment, the system 60 includes a sunscreen formulation 48 including an active ingredient (not shown) configured to absorb ultraviolet electromagnetic radiation; and a marker (not shown) configured to absorb ultraviolet electromagnetic radiation and configured to generate a detectable signal in response to the marker absorbing ultraviolet electromagnetic radiation 26; an interrogator 10 configured to generate interrogation data based on a detectable signal 28 generated by the marker in response to ultraviolet electromagnetic radiation 26 absorbed by the marker; and an analyzer 30 communicatively coupled to the interrogator 10 and configured to receive the interrogation data from the interrogator 10, wherein the analyzer 30 is configured to generate an ultraviolet absorbance analysis based at least in part on the interrogation data.

In the illustrated embodiment, the sunscreen formulation 48 is disposed on the skin of a subject 40. Ultraviolet electromagnetic radiation 26 is shown irradiating upon the sunscreen formulation 48 and in response to the sunscreen formulation 48 absorbing the irradiation 26, the sunscreen formulation 48 generates a detectable signal 28.

The sunscreen formulation can be any sunscreen formulation described herein. In an embodiment, the sunscreen formulation includes an active ingredient configured to absorb ultraviolet electromagnetic radiation; and a marker configured to absorb ultraviolet electromagnetic radiation 26 and configured to generate a detectable signal 28 in response to the marker absorbing ultraviolet electromagnetic radiation 26. In an embodiment, the active ingredient is configured to absorb light in a first range of ultraviolet electromagnetic radiation, and wherein the marker is configured to absorb light in a second range ultraviolet electromagnetic radiation overlapping at least in part with the first range of electromagnetic radiation. In an embodiment, the detectable signal 28 includes light emitted by the marker in a third range of electromagnetic radiation.

The system 60 further comprises an interrogator 10 configured to generate interrogation data based on the detectable signal 28 generated by the marker in response to ultraviolet electromagnetic radiation 26 absorbed by the marker. In the illustrated embodiment, the interrogator 10 includes a filter 14 configured to block or segregate signals not included in the detectable signal 28 or not part of a desired portion or aspect of the detectable signal 28. As shown, the filter 14 is configured to permit at least a portion of the detectable signal 28 to pass through to the sensor 12. The sensor 12 is configured to generate interrogation data based on the detectable signal 28 generated by the marker.

In some embodiments, the sensor 12 includes an electromagnetic energy sensor, such as a charge-coupled device (CCD) camera or a complementary metal-oxide-semiconductor (CMOS) camera. In an embodiment, the sensor 12 is configured to detect (e.g., sense, measure, assess, and the like) electromagnetic radiation, such as visible light (having a wavelength in a range from 400 nm to 700 nm), infrared electromagnetic radiation (having a wavelength in a range from 700 nm to 1 mm), UV electromagnetic radiation, and the like. For example, in an embodiment, the sensor 12 includes one or more of optical sensors (e.g., CCD array), optical waveguide sensors, electromagnetic energy sensors, UV sensors, complementary metal-oxide semiconductor (CMOS) sensors, and the like.

Various features of image sensors are well-known to one of ordinary skill in the art and will not be discussed in detail here. In some embodiments, the sensor 12 includes one or more ultraviolet wavelength sensors configured to sense one or more wavelengths of electromagnetic energy within a particular ultraviolet wavelength range.

In some embodiments, the sensor 12 is configured to generate interrogation data based on the sensed detectable signal (e.g., electromagnetic energy generated by the marker in response to the marker absorbing ultraviolet electromagnetic radiation). Representative interrogation data includes data about absorbance of electromagnetic energy by the marker, intensity of sensed detectable signals, a change in an intensity of sensed detectable signals, wavelengths of electromagnetic energy included in the detectable signal, and the like. In one example, the interrogation data is determined from image data of one or more pixels generated by the sensor 12. In other examples, the interrogation data is determined from one or more of a direct wavelength measurement or a measurement and the interrogation data is output as one or more colors in a color model (e.g., the RGB [red, green, blue] color model, the CMY [cyan, magenta, yellow] or CMYK [cyan, magenta, yellow, black] color space, and the like).

The analyzer 30 is communicatively coupled to the interrogator 10 and configured to receive the interrogation data from the interrogator 10. In an embodiment, the analyzer 30 and the interrogator 10 are communicatively coupled via one or more of a wired connection or a wireless connection, as discussed further herein with respect to FIGS. 10A, 10B, and 10C.

In an embodiment, during operation, the analyzer 30 receives interrogation data from the interrogator 10. The analyzer 30 is configured to generate an ultraviolet absorption analysis based at least in part on the interrogation data. In the depicted embodiment, the analyzer 30 includes an application 38 configured to generate the ultraviolet absorption analysis. In some embodiments, the application 38 is configured to perform image processing on the interrogation data to generate the ultraviolet absorption analysis. The ultraviolet absorption analysis includes a recommendation for further ultraviolet protection of the skin of the subject 40. As discussed further herein, in some embodiments, the recommendation for further ultraviolet protection includes one or more of an indication of an area of the subject 40 that is lacking UV protection, an indication of a recommended area of application of sunscreen formulation on the skin of the subject 40, a recommended SPF value of sunscreen or clothing for further ultraviolet protection of the skin of the subject 40, a timing recommendation for reapplying a sunscreen formulation or wearing additional clothing, or any other recommendation.

In the depicted embodiment, the system 60 includes an output 32 in the form of a display. The output 32 is communicatively coupled to components of the analyzer 30, including a processor 60 executing instructions to operate the application 38. The output 32 is configured to receive the ultraviolet absorption analysis and to output the recommendation for further ultraviolet protection of the skin of the subject 40. In an embodiment, the output 32 is configured to indicate, via one or more of a visual, audio, haptic, or a tactile representation, the ultraviolet protection status of a user, ultraviolet protection recommendation information, exposure information, sunscreen coverage information, or the like. In the particular embodiment depicted in FIG. 5, the output 32 outputs an image 42 representative of the subject 40 and the recommendation, which includes an indication of recommended areas 44 of application of sunscreen on the skin of the subject 40. In another embodiment, an image representative of a subject 40 is depicted with areas indicating which areas of the skin of a subject have been covered by the sunscreen formulation 48 that have degraded or otherwise have insufficient active ingredient. Other examples of outputting the recommendation for further ultraviolet protection of the skin of the subject 40 are described below.

Figure 6A:
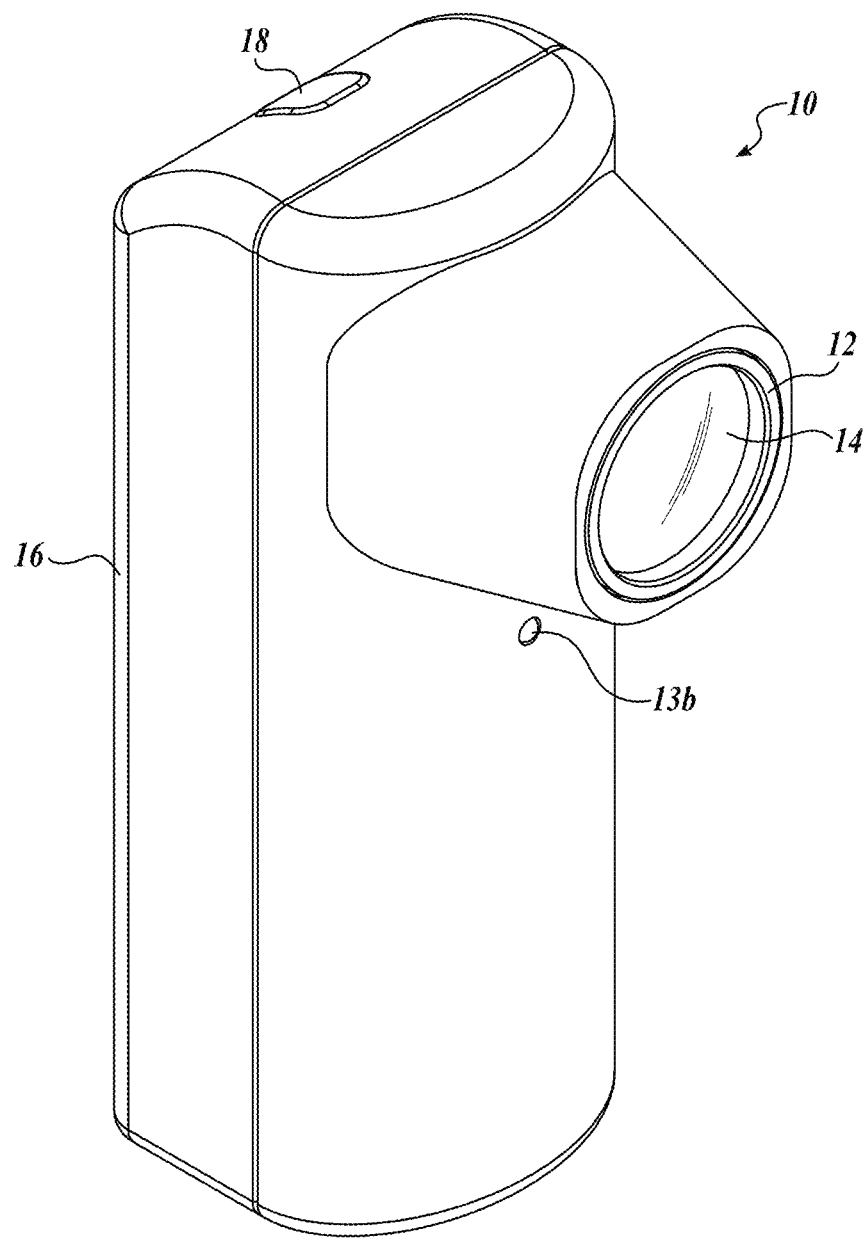
FIGS. 6A to 6C illustrate embodiments of an interrogator, in accordance with an aspect of the disclosure, that includes a sensor.
Figure 6B:
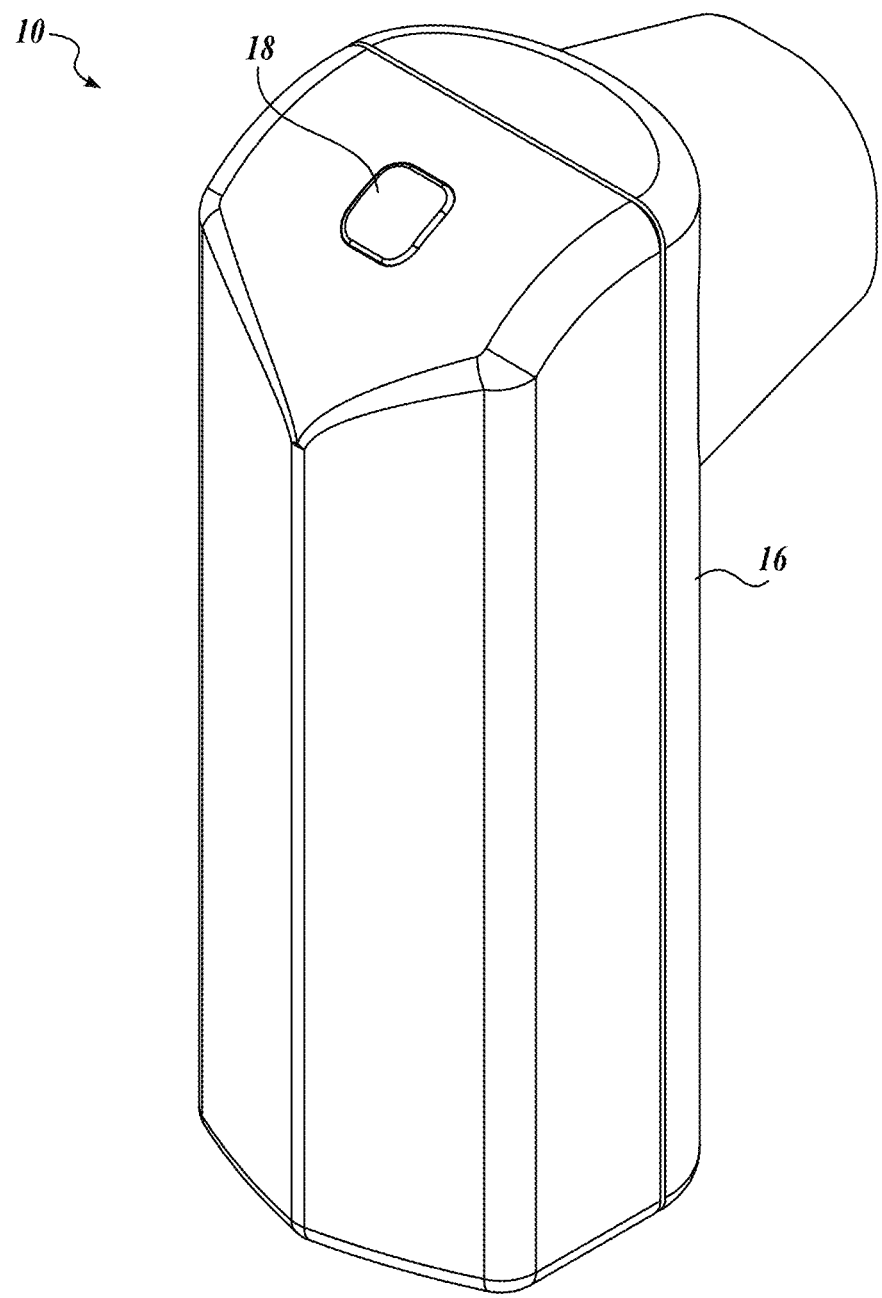
Figure 6C:
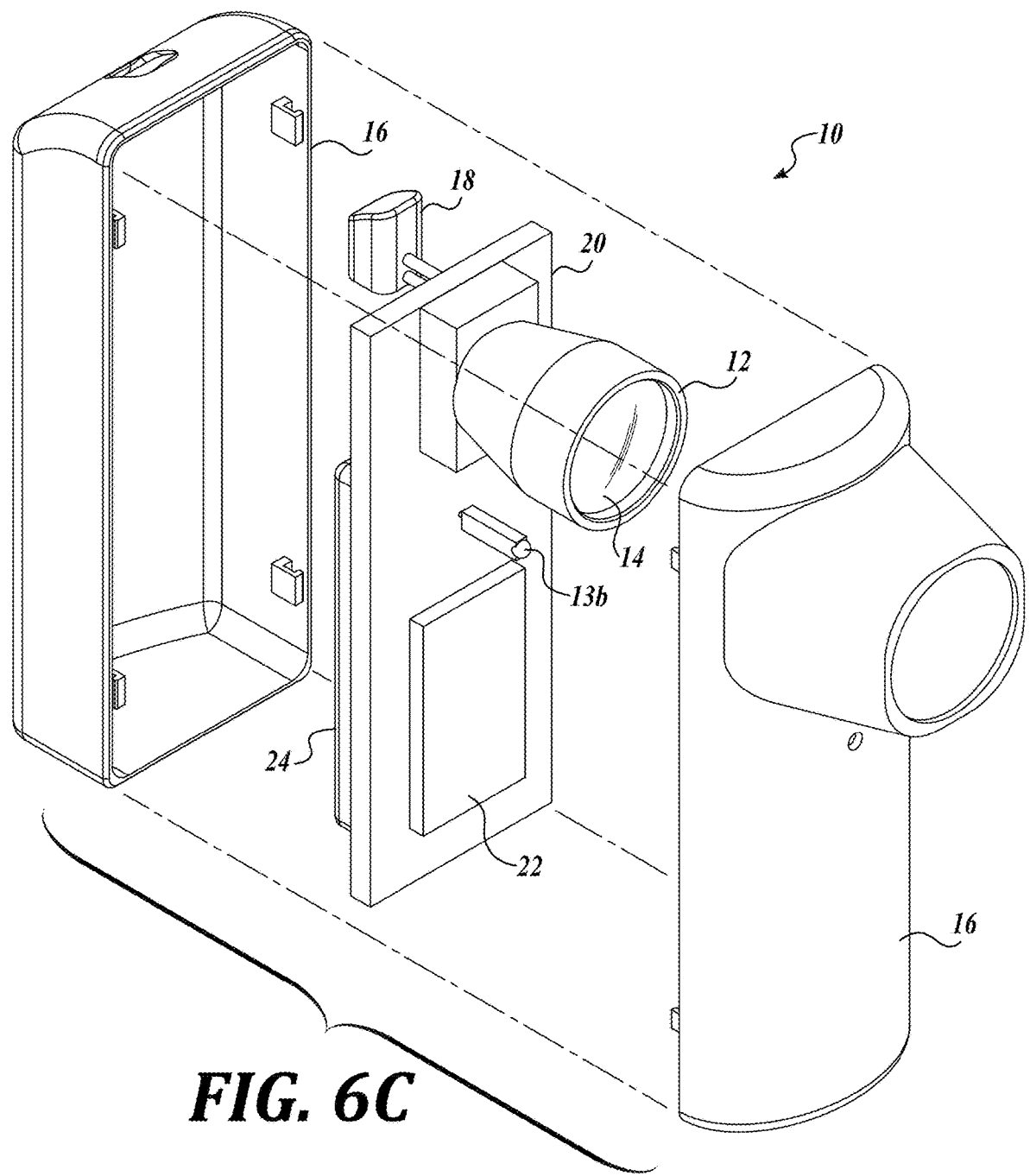

FIGS. 6A, 6B, and 6C depict, respectively, front, side, and exploded views of an embodiment of an interrogator 10. In an embodiment, the interrogator 10 includes a sensor 12. The sensor 12 is configured to sense the detectable signal generated in response to the marker absorbing ultraviolet electromagnetic radiation. In one example, the sensor 12 is configured to sense the detectable signal in response to the marker absorbing ultraviolet electromagnetic radiation from a natural electromagnetic energy source 13a, such as sunlight. In another example, the sensor 12 is configured to sense the detectable signal generated in response to the marker absorbing ultraviolet electromagnetic radiation from an artificial electromagnetic energy source, such as electromagnetic energy source 13b included in the interrogator 10.

The electromagnetic energy source 13 can take a number of forms. In some examples, the electromagnetic energy source 13b includes one or more of a UVA wavelength emitter array or a UVB wavelength emitter array. In one example, the electromagnetic energy source 13b includes one or more Group III-nitride blue LED solid state emitters that are capable of emitting electromagnetic radiation at wavelengths in a range spanning from ultraviolet to blue visible light. In some examples, the number of individual UVA wavelength emitters in the electromagnetic energy source 13b (e.g., the number of LEDs) is in a range from one UVA wavelength emitter to one hundred UVA wavelength emitters.

In one embodiment, the wavelength output of electromagnetic energy source 13 is selected based on a desired response from a particular marker, wherein the electromagnetic energy source 13 emits electromagnetic radiation within an absorbance range of the marker. In one embodiment, the wavelength output of electromagnetic energy source 13b is selected based on a desired response from a particular active ingredient, wherein the electromagnetic energy source 13b emits electromagnetic radiation within an absorbance range of the active ingredient. In one example, the wavelength output of the electromagnetic energy source 13b includes one or more gallium-indium-nitrogen (GaInN) LEDs that have a wavelength output of about 360-370 nm. Such a wavelength output approximates the wavelength output a Wood's lamp examination tool (about 365 nm). In other embodiments, the electromagnetic energy source 13 emits electromagnetic energy in a range of wavelengths from about 10 nm to about 400 nm. In some embodiments, the electromagnetic energy source 13b is configured to emit either a single wavelength based on an absorption peak of a specific active ingredient (e.g., 350 nm) or a plurality of wavelengths within an absorbance spectrum (e.g., a plurality of wavelengths between about 10 nm and about 400 nm) of a particular active ingredient.

In some embodiments, including the one depicted in FIGS. 6A to 6C, the interrogator 10 includes a filter 14 configured to selectively filter electromagnetic energy of particular wavelengths, such as those not included in the detectable signal. In one example, the filter 14 is configured to selectively block wavelengths of electromagnetic energy outside of the range from about 10 nm to about 400 nm such that most or all of the electromagnetic energy reaching the sensor 12 is UV electromagnetic radiation. In other embodiments, the interrogator 10 includes a digital filter configured to filter the interrogation data generated by the sensor 12, such as filtering out interrogation data that is unrelated to detection of detectable signal 28 so that the filtered interrogation data is representative of the detectable signal 28 detected by the sensor 12.

In some embodiments, the detectable signal generated in response to the marker absorbing ultraviolet electromagnetic radiation includes UV electromagnetic radiation. In such a case, the sensor 12 is configured to sense UV electromagnetic radiation. In one example, the filter 14 is configured to filter out electromagnetic radiation that is not UV electromagnetic radiation so that UV electromagnetic radiation associated with detectable signal 28 is received by the sensor 12. In one embodiment, the sensor 12 includes an ultraviolet sensitive camera and the filter 14 is an ultraviolet band-pass filter configured to filter wavelengths that are outside of a particular ultraviolet wavelength range (e.g., outside of a range between about 260 nm and about 400 nm).

In other embodiments, the detectable signal 28 generated in response to the marker absorbing ultraviolet electromagnetic radiation includes electromagnetic radiation outside of the UV electromagnetic energy range. For example, one or more components of the marker may photo-luminesce at a wavelength outside of the UV electromagnetic energy range in response to absorbing UV electromagnetic energy. In such cases, the sensor 12 is configured to sense electromagnetic energy outside of the UV electromagnetic energy range, such as in the visible or infrared range of electromagnetic energy range.

In the embodiment shown in FIGS. 6A to 6C, the interrogator 10 includes a housing 16 that forms a handle. The handle increases convenience for a user to use the interrogator 10. In one embodiment, the housing 16 houses additional components of the interrogator 10. As shown in FIGS. 6A to 6C, the housing 16 provides an opening for a power switch 18 configured to permit a user to toggle power to the interrogator 10 and an opening for the electromagnetic energy source 13b. As shown in FIG. 6C, the housing 16 houses a printed circuit board 20 that includes the electromagnetic energy source 13b, the power switch 18, a wireless communication device 22 and a power source 24 (e.g., rechargeable battery). In other embodiments, the housing 16 houses an electrical connection usable to recharge the power source 24, user input mechanisms other than the power switch 18, indicators and/or displays, and the like.

Figure 7A:
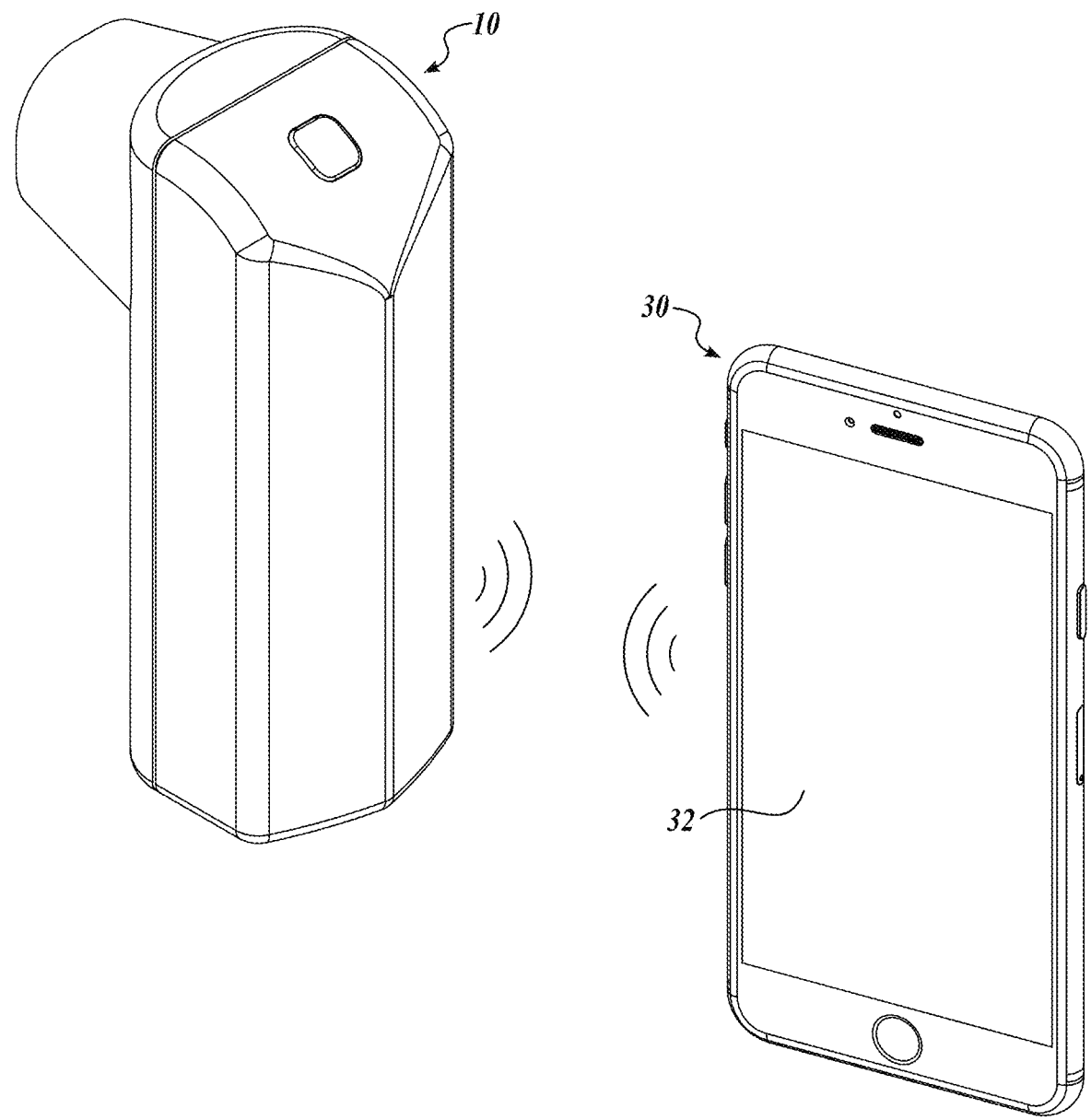
FIGS. 7A to 7C illustrate embodiments of an interrogator device communicatively coupled to an analyzer in accordance with an aspect of the disclosure.
Figure 7B:
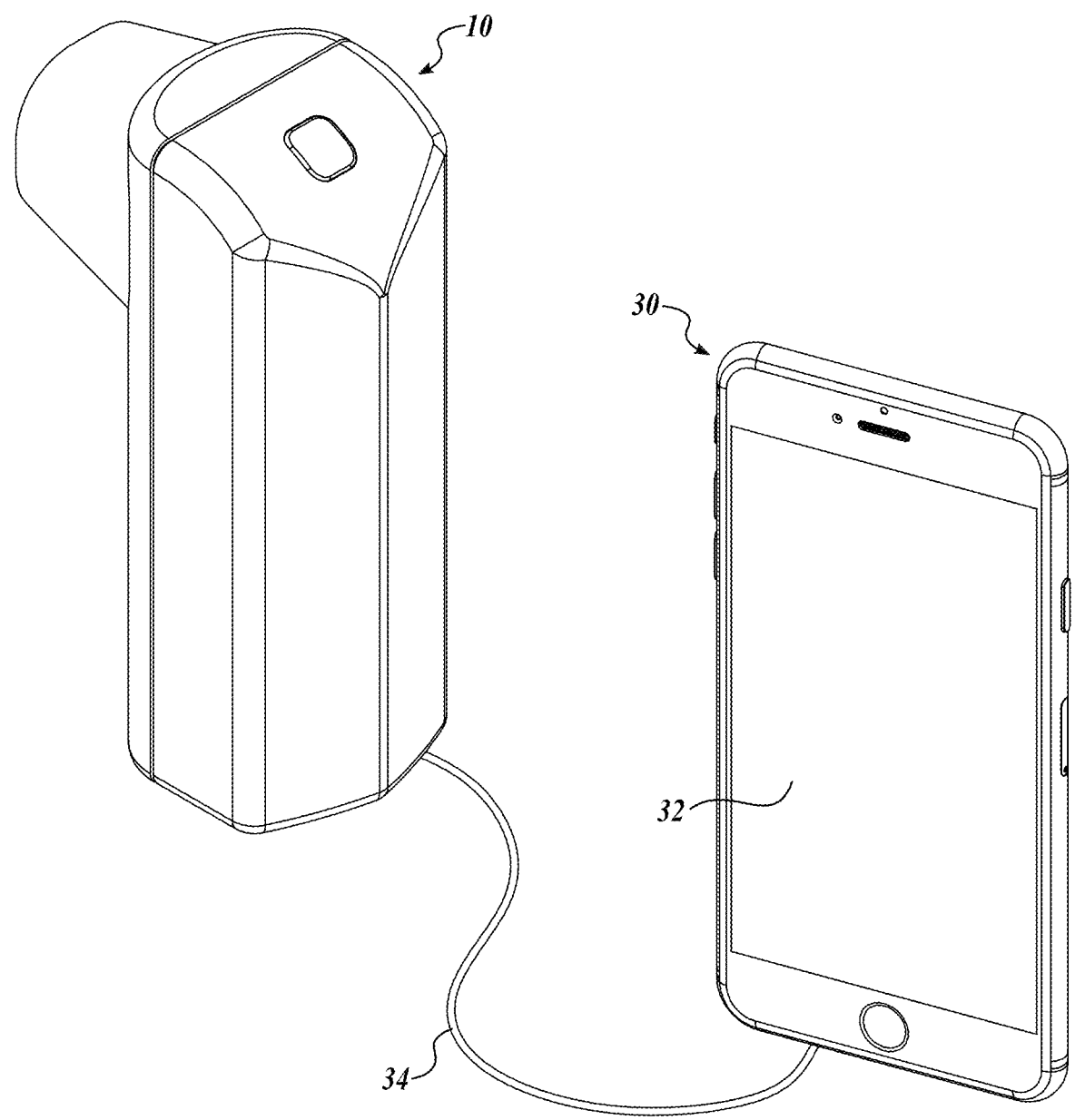
Figure 7C:
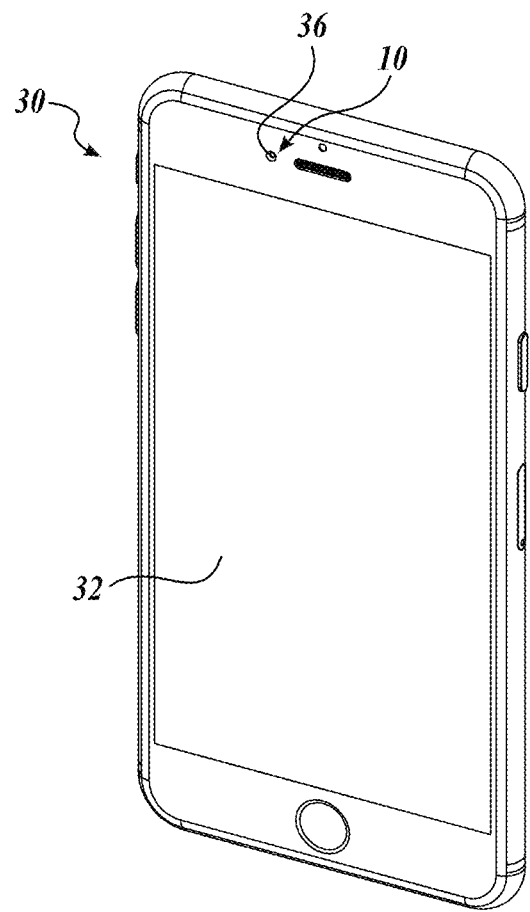

In the embodiments described herein, the analyzer 30 is communicatively coupled to the interrogator 10 and configured to receive the interrogation data from the interrogator 10. Depicted in FIGS. 7A to 7C are examples of the interrogator 10 communicatively coupled to the analyzer 30. In FIGS. 7A to 7C, the analyzer 30 is depicted as a cell phone; however, in other examples, the analyzer 30 takes the form of any number of other computing devices, such as a server, a desktop computer, a laptop computer, a tablet computer, and the like. In the depicted embodiments, the analyzer 30 includes an output 32 in the form of an integrated display. In other embodiments, the output 32 is a monitor coupled to the analyzer 30, a speaker coupled to the analyzer 30, or any other device configured to produce an output.

In FIG. 7A, the interrogator 10 is communicatively coupled to the analyzer 30 via a wireless connection. In some embodiments, the wireless connection is a direct wireless connection, such as a Bluetooth connection, a near field communication (NFC) connection, a direct WiFi connection, or any other direct wireless connection. In some embodiments, the wireless connection is an indirect connection via one or more wireless networks, such as a cellular network (e.g., 4G, LTE), a WiFi network, a local area network, any other network, or any combination thereof. In some embodiments, the wireless connection permits the analyzer 30 to be located remotely from the interrogator 10.

In FIG. 7B, the interrogator 10 is communicatively coupled to the analyzer 30 via a wired connection in the form of a cable 34. In some embodiments, the wired connection permits serial and/or bus communication between the interrogator 10 and the analyzer 30, such as a universal serial bus (USB) connection. In some embodiments not depicted in FIGS. 7A and 7B, the interrogator 10 is communicatively coupled to the analyzer 30 via a combination of wired and wireless connections. In one example, the interrogator 10 is coupled to a WiFi access point via a wireless WiFi connection and the WiFi access point is coupled to the analyzer 30 via a wired LAN connection.

Depicted in FIG. 7C the interrogator 10 and output 32 are integrated into the analyzer 30. In the particular illustrated embodiment, the interrogator 10 is in the form of a forward-facing camera 36 on the analyzer 30. In other examples, the interrogator 10 is a rearward-facing camera on the analyzer 30. In another example, the interrogator 10 includes a sensor 12 separate from a forward-facing and/or rearward-facing visible light camera on the analyzer 30. In some embodiments, where the interrogator 10 is integrated into the analyzer 30, as shown in FIG. 7C, the interrogator 10 is communicatively coupled to the analyzer 30 via internal wiring or circuitry in the analyzer 30.

Figure 8:
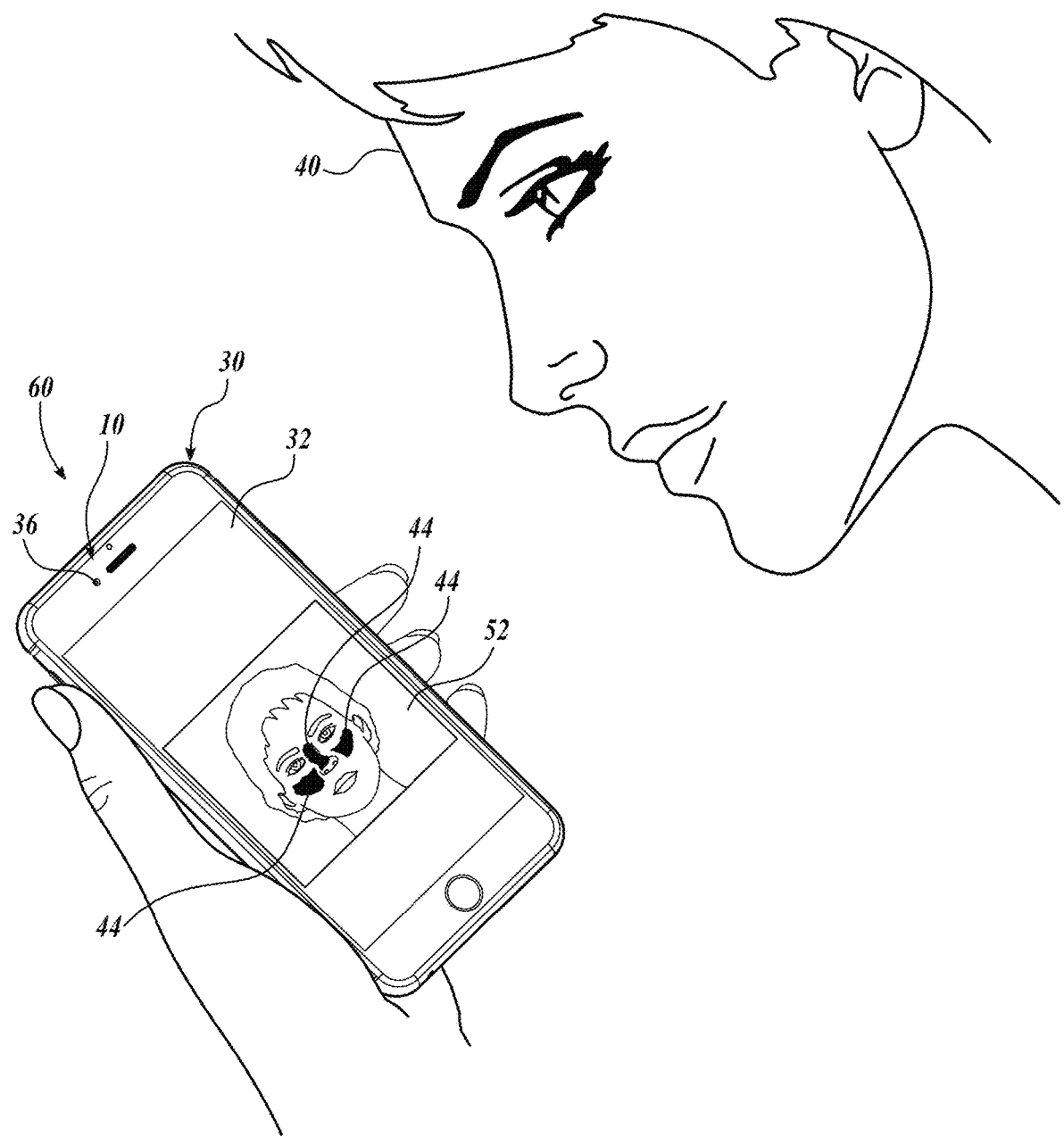
FIG. 8 illustrates another system, in accordance with an aspect of the disclosure, including an output configured to display a recommendation for further ultraviolet protection of the skin of a subject.

One embodiment of presenting a subject with both a visible light image and a recommendation for further ultraviolet protection of the subject's skin is depicted in FIG. 8. In the illustrated embodiment, the interrogator 10 and output 32 are integrated into the analyzer 30 and the interrogator 10 includes a user-facing camera 36 on the analyzer 30. The interrogator 10 is configured to generate interrogation data based on sensed detectable signal 28. The analyzer 30 receives the interrogation data from the interrogator 10, and the analyzer 30 generates an ultraviolet absorption analysis, including at least a recommendation for further ultraviolet protection of the subject's skin, based at least in part on the interrogation data.

The system 60 includes the output 32 in the form of a display. The output 32 displays an image 52. In the particular recommended image shown in FIG. 8, the output 32 outputs a recommendation for further ultraviolet protection of the skin of the subject 40 by highlighting areas 44 of the skin of the subject 40 that are not protected by UV protection or have insufficient UV protection, such as portion of the skin of a subject 40 where the active ingredient in the sunscreen formulation 48 has degraded.

While many of the recommendations for further ultraviolet protection shown above have been image-based recommendations, other non-image-based recommendations can be presented to a user. Some examples of non-image recommendations are depicted in FIGS. 9A and 9B, in the form of efficacy percentages.

Figure 9A:
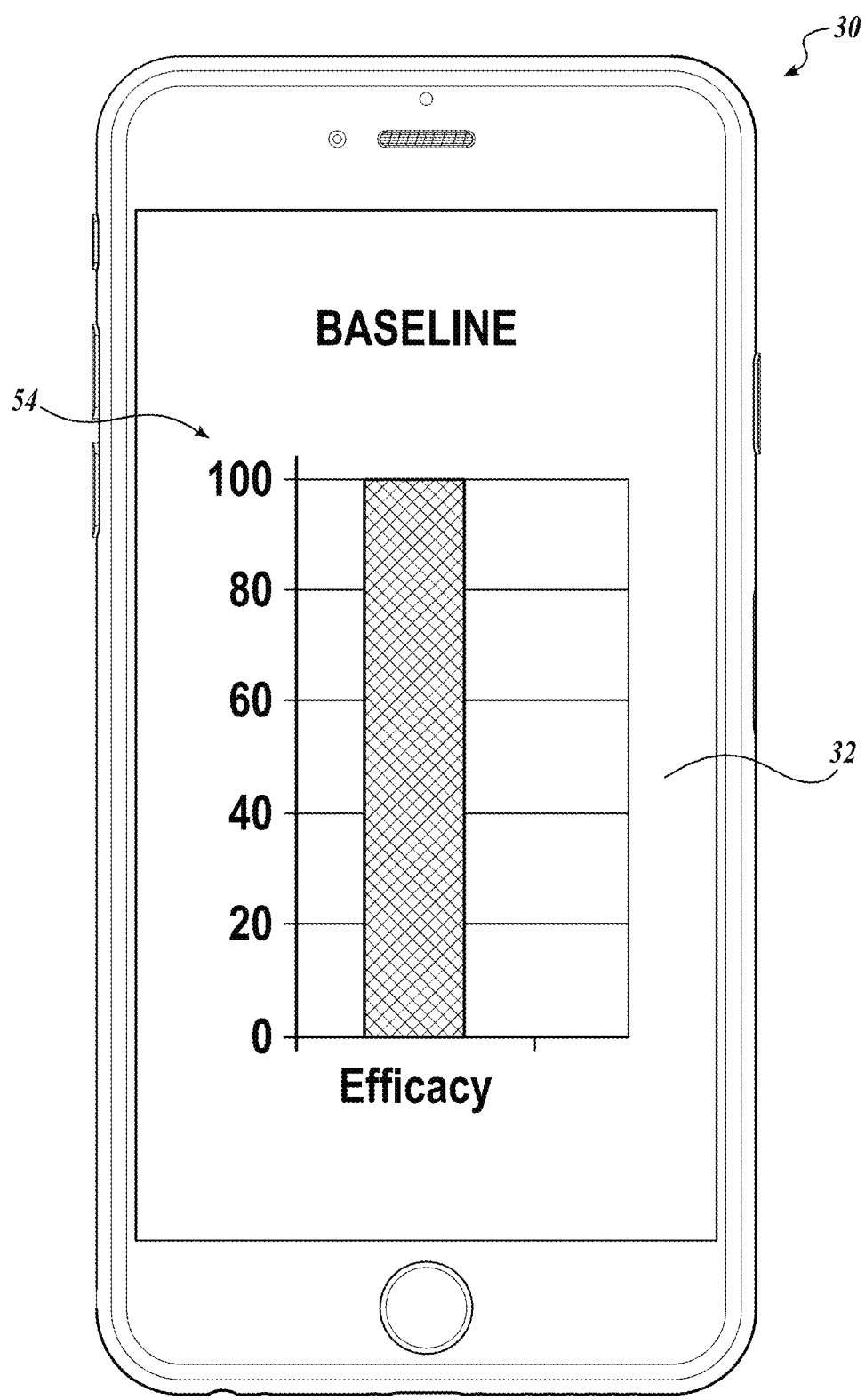
FIGS. 9A and 9B illustrate another system, in accordance with an aspect of the present disclosure, including an output configured to display non-image-based ultraviolet recommendations in the form of efficacy percentages.
Figure 9B:
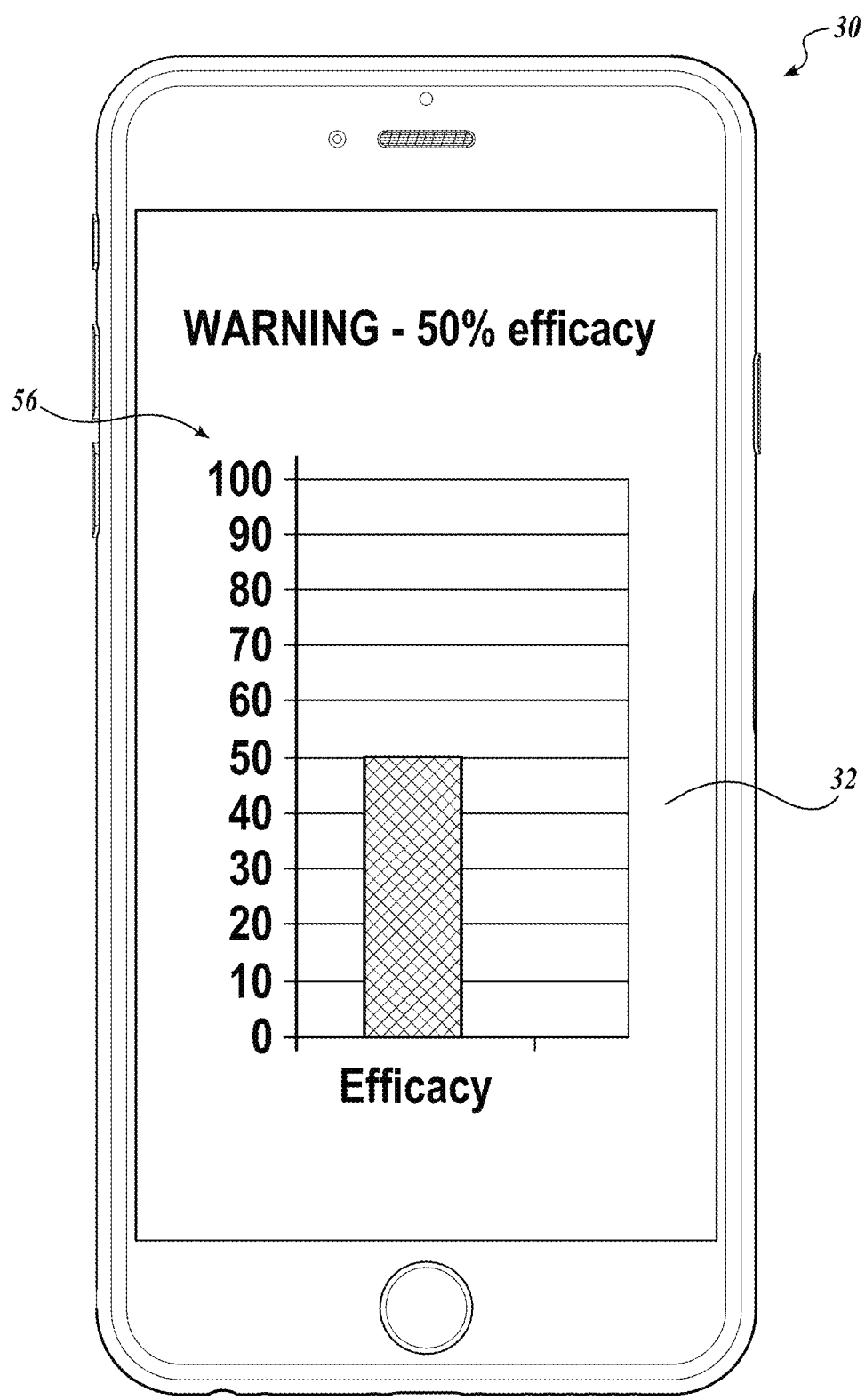

In FIGS. 9A and 9B, efficacy percentages 54 and 56 of UV protection are shown on an output 32 of system 60. Specifically, the efficacy percentage 54 in FIG. 9A indicates that, at that point in time, the level of UV protection is approximately 100% of a baseline UV protection. In some examples, the baseline UV protection is either a measured level of UV protection (e.g., at a time soon after sunscreen formulation 48 is first applied) or a predetermined set of baseline data for typical UV protection (e.g., an expected baseline for a particular sunscreen formulation 48, an expected baseline for a particular SPF rating for sunscreen formulation 48, etc.) based on a level of sensed detectable signal 28.

The efficacy percentage 56 in FIG. 9B indicates that, at that point in time, the level of UV protection is approximately 50% of the baseline UV protection. In the embodiment shown in FIG. 9B, the efficacy percentage 56 also includes a warning about the efficacy percentage 56. In some embodiments, the efficacy percentage 56 is based on one or more of a measurement of UV protection using the interrogator 10.

In an embodiment, the analyzer 30 includes circuitry configured to generate recommendations about changes to the subject's form of UV protection. In one example, the analyzer 30 is configured to compare the current UV protection of a subject to a predetermined level of protection. For example, if the sunscreen formulation 48 is applied to the skin of a subject 40, and the subject's 40 measured level of UV protection is below the predetermined level of protection (i.e., detectable signal 28 above a predetermined level), the recommendation may include a recommendation to increase the level of SPF used by the subject 40 or to reapply the sunscreen formulation 48.

Figure 10B:
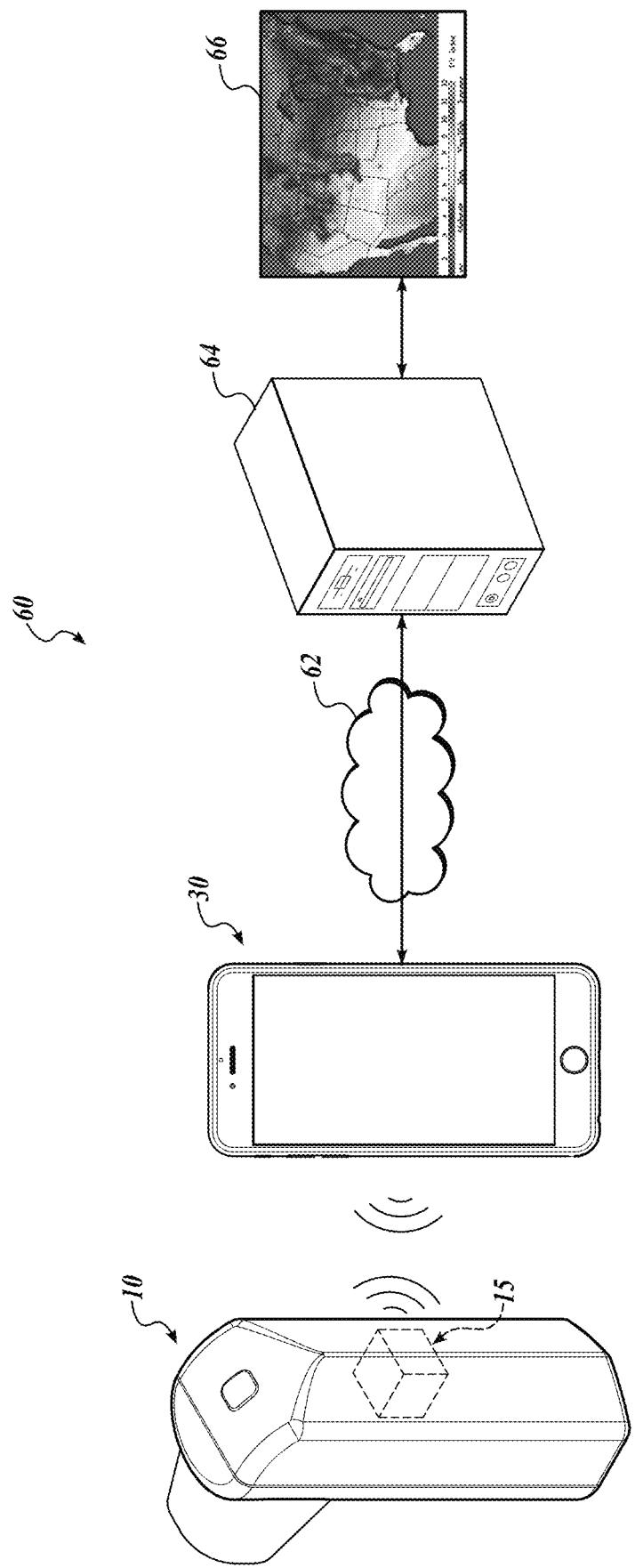

In some embodiments described herein, the analyzer 30 is configured to communicate with a remote computing device. For example, during operation, in an embodiment, the analyzer 30 is configured to implement a discovery protocol that allows the analyzer 30 and a remote client device to find each other and negotiate one or more pre-shared keys. Depicted in FIGS. 10A and 10B are embodiments of systems 60 that include the interrogator 10, the analyzer 30, a communication network 62, and a remote computing device 64 (e.g., a server). In some embodiments, the communication network 62 includes one or more of a cellular network (e.g., 4G, LTE), a WiFi network, a local area network, any other network, or any combination thereof.

In FIG. 10A, the analyzer 30 is configured to send data to the remote computing device 64 via the communication network 62. In some embodiments, analyzer 30 receives interrogation data from the interrogator 10. In some embodiments, the analyzer 30 sends the interrogation data to the remote computing device 64 via the communication network 62. In other embodiments, after the analyzer 30 generates the ultraviolet absorption analysis from the interrogation data, the analyzer 30 sends the ultraviolet absorption analysis to the remote computing device 64 via the communication network 62. In some embodiments, the analyzer 30 sends other data, such as location data about the analyzer 30, atmospheric data taken by the analyzer 30 (e.g., temperature, humidity, etc.), or any other data. In some embodiments where the analyzer 30 sends location data, the analyzer 30 includes a location data acquisition device (e.g., a global positioning system (GPS) device) configured to determine location data associated with one or more of the interrogator 10 or the analyzer 30.

In some embodiments, the remote computing device 64 is configured to maintain information about UV exposure to particular subjects over time. For example, in an embodiment, the remote computing device 64 is configured to maintain user-specific lifetime UV exposure information. In one example, the remote computing device 64 maintains information about actual measured interrogation data about the subject sent to the remote computing device 64 from the analyzer 30. At times when actual measurement data is not available, such as when the analyzer 30 does not provide interrogation data about the subject, the remote computing device 64 may estimate an amount of UV exposure for the subject. Such an estimate may be based on the location of the analyzer 30 (e.g., whether the subject is indoors or outdoors), a speed of the analyzer 30 (e.g., whether the subject is outside or in a vehicle), the atmospheric data near the analyzer 30, or any other type of data. Over time, the remote computing device 64 may compile an estimated UV exposure level for a particular subject. Any estimated UV exposure level for a particular subject may be useful to the subject in determining whether to limit UV exposure in the future, to medical providers in determining whether the subject is at increased risk for particular conditions (e.g., skin cancer), to insurance providers to better assess the risk of the subject's future medical conditions, and the like.

In the embodiment shown in FIG. 10B, the remote computing device 64 is in communication with a weather database 66. In some embodiments, the weather database 66 is stored locally on the remote computing device 64. In other embodiments, the weather database 66 is located remotely (e.g., the National Climactic Data Center database). In some embodiments, the weather database 66 includes historical data about particular locations and the remote computing device 64 is configured to determine atmospheric data of locations of the analyzer 30 over time. Such information about atmospheric data of locations of the analyzer 30 over time may increase the accuracy of any estimates about UV exposure to a subject in the absence of actual measured data.

Figure 10C:
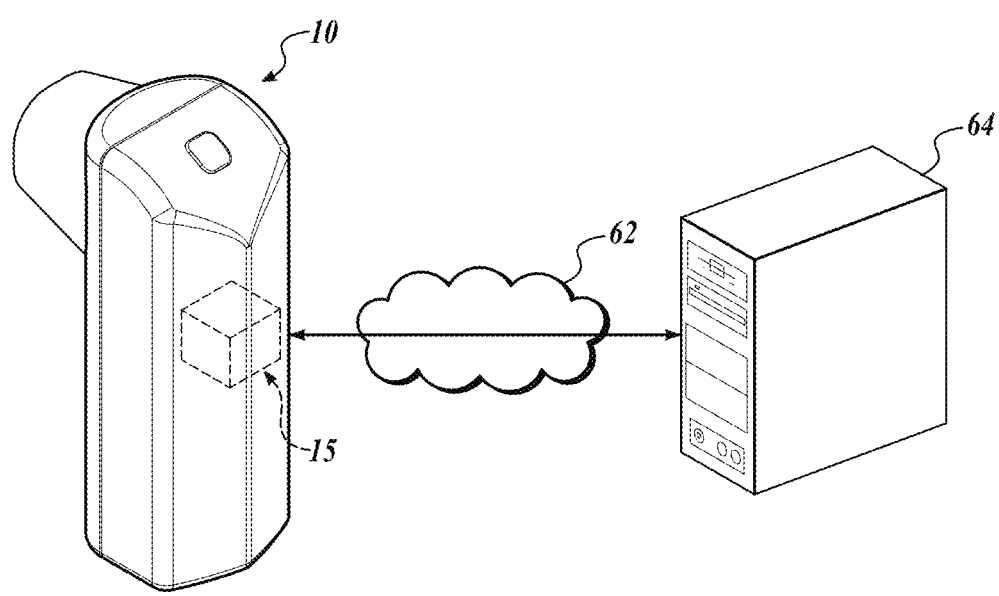
FIG. 10C illustrates another system, in accordance with an aspect of the disclosure, including an interrogator, a communication network, and a remote computing device.

Another embodiment of a system 60 that includes the interrogator 10, the communication network 62, and the remote computing device 64 is depicted in FIG. 10C. As depicted, the interrogator 10 is configured to communicate with the computing device 64 via the communication network 62. In this embodiment, the interrogator 10 sends interrogation data to the remote computing device 64 via the communication network 62. The remote computing device 64 operates as an analyzer to receive the interrogation data from the interrogator and generate an ultraviolet absorption analysis, including at least a recommendation for further ultraviolet protection of the subject's skin, based at least in part on the interrogation data. The remote computing device 64 is configured to send the ultraviolet absorption analysis to an output associated with the interrogator 10. In one embodiment, the interrogator 10 includes an output 32 (e.g., a display or a speaker) which is configured to output the recommendation for further ultraviolet protection of the subject's skin.

The configuration in FIG. 10C allows for the analyzer (e.g., remote computing device 64) to be located remotely from the interrogator 10. In such a case, the analyzer (e.g., remote computing device 64) is configured to store one or more of data about sensed electromagnetic energy of the subject's skin received from the interrogator over a period of time covering more than one day or location data about the location of the subject received from the interrogator over a period of time covering more than one day.

In another aspect, the present disclosure provides a system for analyzing ultraviolet protection for skin of a subject. In an embodiment, the system includes marker acquisition means for receiving sunscreen marker information responsive to a marker absorbing ultraviolet electromagnetic radiation; ultraviolet analysis means for generating an ultraviolet absorption analysis based at least in part on the sunscreen marker information; and protection display means for generating a virtual display including one or more instances indicative of an ultraviolet protection status of a user, ultraviolet protection recommendation information, exposure information, and sunscreen coverage information analysis based at least in part on the ultraviolet absorption analysis.

In an embodiment, the marker acquisition means includes at least one of a transceiver, a transmitter, and a receiver 15 operably coupled to an interrogator having at least one electromagnetic energy transducer configured to acquire sunscreen marker information responsive to a marker absorbing ultraviolet electromagnetic radiation. In an embodiment, the interrogator includes a sensor chosen from an ultraviolet sensor, an optical sensor, a radiation sensor, and a camera. In an embodiment, the marker acquisition means includes an interrogator, such as interrogator 12 of system 60.

In an embodiment, sunscreen marker information is chosen from a marker intensity, a change in marker intensity, a marker intensity maximum, and a change in a marker intensity maximum.

In an embodiment, the ultraviolet analysis means include sunscreen marker information stored in memory and at least one processor. In an embodiment, the processor is configured to determine at least one of an ultraviolet protection status of a user, ultraviolet protection recommendation information, exposure information, and sunscreen coverage information based on one or more inputs indicative of sunscreen marker information. In an embodiment, the ultraviolet analysis means include analyzer 10 of system 60.

In an embodiment, the protection display means include a display operably coupled to a processor configured to generate a virtual representation on the display. In an embodiment, the processor is configured to generate on the display a virtual representation including one or more instances indicative of an ultraviolet protection status of a user. In an embodiment, the processor is configured to generate on the display a virtual representation including one or more instances indicative of ultraviolet protection recommendation information. In an embodiment, the processor is configured to generate on the display a virtual representation including one or more instances indicative of exposure information. In an embodiment, the processor is configured to generate on the display a virtual representation including one or more instances indicative of sunscreen coverage information analysis based at least in part on the ultraviolet absorption analysis.

In an embodiment, the display is a touch screen display. In an embodiment, the display includes one or more of a smart phone screen, a desktop computer screen, a laptop computer screen, a television screen, and a tablet screen. In an embodiment, the display includes output 32.

In another aspect, the present disclosure provides method of analyzing ultraviolet protection of skin of a subject. In an embodiment, the method comprises receiving, by an analyzer from an interrogator, interrogation data generated by the interrogator, interrogation data based on sensed detectable signal generated by a marker in a sunscreen formulation in response to the marker absorbing ultraviolet electromagnetic radiation; and generating, by the analyzer, an ultraviolet absorption analysis based at least in part on the interrogation data.

In an embodiment, the sunscreen formulation is according to any sunscreen formulation described herein. In an embodiment, the sunscreen formulation comprises an active ingredient configured to absorb light in a first range of ultraviolet electromagnetic radiation, wherein the marker is configured to absorb light in a second range ultraviolet electromagnetic radiation overlapping at least in part with the first range of electromagnetic radiation and configured to generate a detectable signal when the marker absorbs light in the second range of ultraviolet electromagnetic radiation.

In an embodiment, the method uses a system as described further herein, such as system 60, wherein the analyzer is analyzer 30 and the interrogator is interrogator 10.

In an embodiment, the ultraviolet absorption analysis includes at least a recommendation for further ultraviolet protection of the skin of a subject. In an embodiment, the method further comprising sending, by the analyzer, the ultraviolet analysis with the recommendation for further ultraviolet protection of the skin of a subject to an output, wherein the output is configured to receive the ultraviolet analysis and to output the recommendation for further ultraviolet protection of the skin of a subject.

In an embodiment, generating the ultraviolet absorption analysis includes generating the recommendation for further ultraviolet protection of the skin of a subject based on an amount of the detectable signal sensed by the interrogator. In an embodiment, generating the ultraviolet analysis includes generating the recommendation for further ultraviolet protection of the skin of a subject based on a comparison of an amount of the detectable signal sensed by the interrogator at first time and an amount of the detectable signal sensed by the interrogator at second time after the first time.

It should be noted that for purposes of this disclosure, terminology such as "upper," "lower," "vertical," "horizontal," "inwardly," "outwardly," "inner," "outer," "front," "rear," etc., should be construed as descriptive and not limiting the scope of the claimed subject matter. Further, the use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings. The term "about" means plus or minus 5% of the stated value.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The embodiments of the invention in which an exclusive property or privilege is claimed are defined as follows:

1. A system for analyzing ultraviolet protection of skin of a subject, the system comprising:
   a sunscreen formulation for application to skin of a subject, the sunscreen formulation comprising:
      an active ingredient configured to absorb ultraviolet electromagnetic radiation; and
      a marker configured to absorb the ultraviolet electromagnetic radiation and configured to generate a detectable signal in response to the marker absorbing the ultraviolet electromagnetic radiation;
      wherein the active ingredient is configured to absorb light in a first range of the ultraviolet electromagnetic radiation, and wherein the marker is configured to absorb light in a second range of the ultraviolet electromagnetic radiation overlapping at least in part with the first range of the ultraviolet electromagnetic radiation,
   an interrogator configured to generate interrogation data based on the detectable signal generated by the marker in response to the ultraviolet electromagnetic radiation absorbed by the marker; and
   an analyzer communicatively coupled to the interrogator and configured to receive the interrogation data from the interrogator, wherein the analyzer is configured to generate an ultraviolet absorption analysis based at least in part on the interrogation data,
   wherein generating the ultraviolet absorption analysis includes generating ultraviolet protection recommendation information based on an amount of the detectable signal sensed by the interrogator, and
   wherein, when the marker generates the detectable signal at a second level greater than a first level in response to the sunscreen formulation absorbing additional ultraviolet electromagnetic radiation, the analyzer generates a recommendation for further ultraviolet protection of the skin of the subject.

2. The system of claim 1, wherein the detectable signal includes light emitted by the marker in a third range of electromagnetic radiation and the interrogator includes a sensor including a photo-detector configured to absorb the light emitted by the marker and a band-pass filter configured to filter wavelengths that are outside of the third range of electromagnetic radiation.

3. The system of claim 1, wherein the ultraviolet absorption analysis includes at least a recommendation for further ultraviolet protection of the skin of a subject, wherein the recommendation for further ultraviolet protection of the skin of the subject includes a recommended area of application of the sunscreen formulation on the skin of the subject.

4. The system of claim 1, wherein the ultraviolet absorption analysis includes at least a recommendation for further ultraviolet protection of the skin of a subject, the system further comprising an output communicatively coupled to the analyzer and configured to receive the ultraviolet absorption analysis and to output the recommendation for further ultraviolet protection of the skin of the subject.

5. The system of claim 4, wherein the output is configured to display an image of the skin of the subject with the recommended area of application of sunscreen highlighted in a particular color.

6. A system for analyzing ultraviolet protection for skin of a subject, the system comprising:
   a sunscreen formulation comprising:
      an active ingredient configured to absorb ultraviolet electromagnetic radiation; and
      a marker configured to absorb the ultraviolet electromagnetic radiation and configured to generate a detectable signal in response to the marker absorbing the ultraviolet electromagnetic radiation, wherein the active ingredient is configured to absorb light in a first range of the ultraviolet electromagnetic radiation; and wherein the marker is configured to absorb light in a second range of the ultraviolet electromagnetic radiation overlapping at least in part with the first range of the ultraviolet electromagnetic radiation;
   marker acquisition means for receiving sunscreen marker information responsive to the marker absorbing the ultraviolet electromagnetic radiation;
   ultraviolet analysis means for generating an ultraviolet absorption analysis based at least in part on the sunscreen marker information; and
   protection display means for generating a virtual display including one or more instances indicative of an ultraviolet protection status of a user, ultraviolet protection recommendation information, exposure information, or sunscreen coverage information analysis based at least in part on the ultraviolet absorption analysis,
   wherein generating the ultraviolet absorption analysis includes generating the ultraviolet protection recommendation information based on an amount of the detectable signal sensed by the marker acquisition means, and
   wherein when the marker generates the detectable signal at a second level greater than a first level in response to the sunscreen formulation absorbing additional ultraviolet electromagnetic radiation, the ultraviolet analysis means generates a recommendation for further ultraviolet protection of the skin of the subject.

7. The system of claim 6, wherein the marker acquisition means includes at least one of a transceiver, a transmitter, and a receiver operably coupled to an interrogator having at least one electromagnetic energy transducer configured to acquire sunscreen marker information responsive to a marker absorbing ultraviolet electromagnetic radiation.

8. The system of claim 7, wherein the at least one electromagnetic energy transducer is chosen from an ultraviolet sensor, an optical sensor, a radiation sensor, and a camera.

9. The system of claim 6, wherein the ultraviolet analysis means includes sunscreen marker information stored in memory and at least one processor configured to determine at least one of the ultraviolet protection status of a user, the ultraviolet protection recommendation information, the exposure information, and the sunscreen coverage information based on one or more inputs indicative of sunscreen marker information.

10. The system of claim 6, wherein the protection display means includes a touch screen display operably coupled to a processor configured to generate a virtual representation on the touch screen display including one or more instances indicative of the ultraviolet protection status of a user, the ultraviolet protection recommendation information, the exposure information, or the sunscreen coverage information analysis based at least in part on the ultraviolet absorption analysis.

* * * * *